US 9,267,845 B2

(12) United States Patent
Ichijyo et al.

(10) Patent No.: US 9,267,845 B2
(45) Date of Patent: Feb. 23, 2016

(54) APPARATUS FOR COUNTING VIABLE PARTICLES IN LIQUID IN REAL TIME, DIALYSIS FLUID MONITORING SYSTEM AND PURIFIED WATER MONITORING SYSTEM USING THE APPARATUS, AND METHOD OF COUNTING VIABLE PARTICLES IN LIQUID IN REAL TIME

(71) Applicant: RION CO., LTD., Kokubunji-shi, Tokyo (JP)

(72) Inventors: Kazuo Ichijyo, Tokyo (JP); Kazuma Sekimoto, Tokyo (JP); Kousei Sekigawa, Tokyo (JP); Yukihiro Kimoto, Tokyo (JP); Takayuki Kosaka, Tokyo (JP)

(73) Assignee: RION CO., LTD., Tokyo (JP)

( * ) Notice: Subject to any disclaimer, the term of this patent is extended or adjusted under 35 U.S.C. 154(b) by 0 days.

(21) Appl. No.: 14/292,535

(22) Filed: May 30, 2014

(65) Prior Publication Data
US 2014/0335557 A1 Nov. 13, 2014

Related U.S. Application Data

(63) Continuation of application No. PCT/JP2012/007635, filed on Nov. 28, 2012.

(30) Foreign Application Priority Data

Dec. 5, 2011 (JP) ................................. 2011-265613
Jan. 16, 2012 (JP) ................................. 2012-006107
Jan. 17, 2012 (JP) ................................. 2012-007338

(51) Int. Cl.
*G01J 3/30* (2006.01)
*G01J 3/44* (2006.01)
(Continued)

(52) U.S. Cl.
CPC ............ *G01J 3/4406* (2013.01); *A61M 1/1605* (2013.01); *G01N 15/1459* (2013.01);
(Continued)

(58) Field of Classification Search
CPC .......... G01N 21/6428; G01N 21/6458; G01N 21/6452; G01N 21/645; G01J 3/4406; G01J 3/30
USPC .................................................. 356/300–445
See application file for complete search history.

(56) References Cited

U.S. PATENT DOCUMENTS 4,979,824 A 12/1990 Mathies et al.
2010/0108910 A1 5/2010 Morrell et al.
(Continued)

FOREIGN PATENT DOCUMENTS

EP 2218472 A1 8/2010
JP 08015157 A 1/1996
(Continued)

OTHER PUBLICATIONS

Hidenori Yamamoto et al, The Japanese Journal of Clinical Dialysis, Oct. 10, 2011, vol. 27, No. 11, pp. 1495-1501.
(Continued)

*Primary Examiner* — Abdullahi Nur
(74) *Attorney, Agent, or Firm* — Holtz, Holtz & Volek PC

(57) ABSTRACT

A viable particle counting apparatus 77 includes devices 10, 70, 2. The device 10 radiates a light with a predetermined wavelength toward a liquid containing a detection target. The device 70 reduces a Raman-scattered light emitted from the liquid out of lights emitted due to an interaction of the light radiated by the device 10 with the target or the liquid and selects an autofluorescence light emitted from the target. The device 2 determines whether or not the target contained in the liquid is a viable particle, based on a light obtained after the Raman-scattered light is reduced by the device 70. The device 10 radiates the light with a wavelength that causes the autofluorescence light and the Raman-scattered light to be different in peak wavelength.

15 Claims, 20 Drawing Sheets

(51) Int. Cl.
  *G01N 21/64* (2006.01)
  *A61M 1/16* (2006.01)
  *G01N 15/14* (2006.01)

(52) U.S. Cl.
  CPC ......... *A61M 1/16* (2013.01); *A61M 2205/3306* (2013.01); *G01N 21/645* (2013.01); *G01N 21/6428* (2013.01); *G01N 2015/1486* (2013.01)

(56) References Cited

U.S. PATENT DOCUMENTS

| | | | |
|---|---|---|---|
| 2010/0116647 A1 | 5/2010 | Kornmuller et al. | |
| 2011/0309019 A1 | 12/2011 | Ahrens | |
| 2012/0040330 A1* | 2/2012 | Carpenter | C12Q 1/04 435/3 |

FOREIGN PATENT DOCUMENTS

| | | | |
|---|---|---|---|
| JP | 09105738 A | 4/1997 |
| JP | 2000241335 A | 9/2000 |
| JP | 2007300840 A | 11/2007 |
| JP | 2008039477 A | 2/2008 |
| JP | 2008062201 A | 3/2008 |
| JP | 2009000673 A | 1/2009 |
| JP | 2009501907 A | 1/2009 |
| WO | 9014589 A1 | 11/1990 |
| WO | 2010024963 A1 | 3/2010 |

OTHER PUBLICATIONS

International Search Report and Written Opinion dated Mar. 5, 2013 issued in International Application No. PCT/JP2012/007635.
Partial European Search Report dated Aug. 5, 2015, issued in counterpart European Application No. 12 85 5154.
Japanese Office Action (and English translation thereof) dated Nov. 10, 2015, issued in counterpart Japanese Application No. 2011-265613.
Japanese Office Action (and English translation thereof) dated Nov. 17. 2015, issued in counterpart Japanese Application No. 2012-006107.
Japanese Office Action (and English translation thereof) dated Nov. 17. 2015, issued in counterpart Japanese Application No. 2012-007338.
Extended European Search Report dated Dec. 3, 2015, issued in counterpart European Application No. 12855154.6.

* cited by examiner

ApparatuS FOR COUNTING VIABLE PARTICLES IN LIQUID IN REAL TIME, DIALYSIS FLUID MONITORING SYSTEM AND PURIFIED WATER MONITORING SYSTEM USING THE APPARATUS, AND METHOD OF COUNTING VIABLE PARTICLES IN LIQUID IN REAL TIME

BACKGROUND OF THE INVENTION

1. Field of the Invention

The present invention relates to an apparatus for counting viable particles in a liquid, and in particular, to an apparatus which detects viable particles existing in a liquid in real time.

2. Description of the Related Art

In the detection of viable particles, there have been known a method of cultivation (official analytical method), a micro-colony method, an ATP (luciferase) method, a fluorescent dye method, an autofluorescence method, and so on. Among these detection methods, a detection method enabling to obtain the result on the presence/absence of the viable particles in real time is the autofluorescence method. This autofluorescence method is a detection method of viable particles utilizing an autofluorescence light emitted from the viable particles. A concrete autofluorescence method detects the viable particles by utilizing the following phenomenon. This phenomenon is a phenomenon that, when a light with a predetermined wavelength is first radiated to a given substance, an energy state that this substance has is excited (the substance absorbs the radiated light), and thereafter the substance emits extra energy to the outside as fluorescence at the time of returning to a ground state from the excited state. Further, when irradiated with a light having a wavelength unique to the substance, the substance easily emits an autofluorescence light to the outside. This is because the wavelength easily causing the substance to absorb the light differs depending on each substance.

There is an art to confirm the presence/absence of viable particles based on whether or not an autofluorescence light is detected, by utilizing this autofluorescence phenomenon. For this purpose, in this art, an ultraviolet ray is radiated to a water medium. This art uses a filter that selects a specific part (wavelength band) of the autofluorescence light that is to be measured.

However, when the ultraviolet ray is radiated to the water, a Raman-scattered light by water is also detected in addition to the autofluorescence light. This is because the radiated ultraviolet ray is scattered by the water (Raman scattering). Concretely, the Raman-scattered light longer in wavelength than the radiated ultraviolet ray is emitted. Therefore, it becomes difficult to detect the presence/absence of only the viable particles by using the autofluorescence light as an index. Further, even if the autofluorescence light only whose specific region is selected is detected, it is difficult to detect the presence/absence of the viable particles. This is because the Raman-scattered light which has the same wavelength as that of the autofluorescence light is emitted from the liquid, depending on the wavelength of the radiated ultraviolet ray.

Further, conventionally, in the manufacture of a dialysis fluid administered to a human body, the dialysis fluid is first treated to a state not causing a problem even when administered to a human body, by filtering out viable particles by a filter or the like. Then, regarding the manufactured dialysis fluid, it is inspected whether or not the viable particles exist in the dialysis fluid by an inspection method such as a method of cultivation (official analytical method) or a fluorescent dye method. Further, in blood dialysis to a human body, a dialysis fluid is made to flow in a specific medical instrument and blood having undergone the blood dialysis there is administered to a human body. This flowing dialysis fluid also undergoes a filtration treatment to be manufactured and managed, and similarly undergoes a viable particle inspection.

In the inspection by the method of cultivation, the viable particles in the dialysis fluid are cultivated on a bleeding ground under a condition of low temperature and a long period (several days to one week) and it is confirmed whether or not a colony is formed. In this manner, it is inspected whether or not the viable particles exist. Further, in the inspection by the florescent dye method, a specific dyeing reagent is dropped to the dialysis fluid, and after several-minute dyeing, light is radiated, followed by photographing by a CCD camera or the like, and the number of points emitting light is counted. In this manner, it is determined whether or not the viable particles exist and the number of the viable particles is counted.

Here, when the dialysis fluid inspection is performed by the fluorescent dye method, every time the inspection is performed, it is necessary to move the dialysis fluid to a place different from a place where the blood dialysis is performed, perform the dyeing process by the specific dyeing reagent, and count the number of the viable particles after the photographing by the CCD camera. Further, it takes about twenty minutes to confirm the result of the inspection of the dialysis fluid. Therefore, it is not possible to perform the inspection in real time during the blood dialysis.

Further, conventionally, water sent from a purified water basin provided in a water purification plant, an aquarium, a lake or a marsh, a garden, or the like is purified by filtration, disinfection, or the like in order to purify the water by eliminating and killing viable particles contained in the water. Further, regarding this purified water, it is inspected by a turbidimeter, a fine particle counter, or the like whether or not sterilizing purification of the viable particles is performed efficiently.

For example, in the inspection by the turbidimeter, turbidity is calculated, and from this turbidity, a probability that viable particles in water are eliminated by sterilizing purification is calculated. A concrete inspection method is performed by radiating a light to the water containing particles (viable particles or non-viable particles), and comparing the light radiated from a light source and a scattered light received by a light receiving apparatus, or detecting an interference light due to the particles. Further, by using the fine particle counter, it is confirmed whether or not a specific pathogenic worm (for example, cryptosporidium) in water is eliminated by the sterilizing purification. In a concrete confirmation method, a fluorescent labeled antibody easily bonding with the pathogenic worm being the detection target is mixed with the purified water, and it is confirmed whether or not the water is purified by sterilization based on whether or not a fluorescence light emitted from the detection target is detected.

In this method, the real-time inspection of the water having undergone the purification treatment is not possible. This is because, as the detection method, an antigen-antibody reaction is utilized by using chemicals such as the fluorescent labeled antibody. For example, it takes twenty minutes to thirty minutes at 37° C. or one hour or more at room temperature for the antigen-antibody reaction between cryptosporidium and the fluorescent labeled antibody to end. Further, since the detection target has been purified and thus its amount is only a little, a large amount of the fluorescent labeled antibody is required in order to easily cause the antigen-antibody reaction.

In addition, preliminary arrangements for the inspection such as filtering the water having undergone the purification treatment by using a filter with a 3μ pore size, capturing and condensing large fine particles containing the cryptosporidium on a surface of the filter, and thereafter using the fluorescent labeled antibody are required in advance. Here, when the inspection (detection) of viable particles other than cryptosporidium is performed, it is necessary to use another fluorescent labeled antibody easily undergoing an antigen-antibody reaction with the viable particles. Therefore, the inspection method utilizing the antigen-antibody reaction with the viable particles has problems that it requires a predetermined time to confirm the inspection result, a plurality of kinds of the fluorescent labeled antibodies have to be prepared, and the purified water has to be condensed or a large amount of the fluorescent labeled antibody has to be prepared.

SUMMARY OF THE INVENTION

The inventions disclosed and claimed herein include a viable particle counting apparatus of one embodiment. The counting apparatus includes: a light emitting element which radiates a light with a predetermined wavelength toward a liquid containing a detection target; a device which reduces transmission of a Raman-scattered light emitted from the liquid out of lights emitted due to an interaction of the target or the liquid with the light radiated by the light emitting element and transmits an autofluorescence light emitted from the target; and a determining device which determines whether or not the target contained in the liquid is a viable particle, based on a light obtained after the Raman-scattered light is reduced by the device which selects the autofluorescence light.

Further scope of applicability of the present invention will become apparent from the detailed description given hereinafter. However, it should be understood that the detailed description and specific example, while indicating preferred embodiment of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitative of the present invention, and wherein.

DETAILED DESCRIPTION

Figure 1:
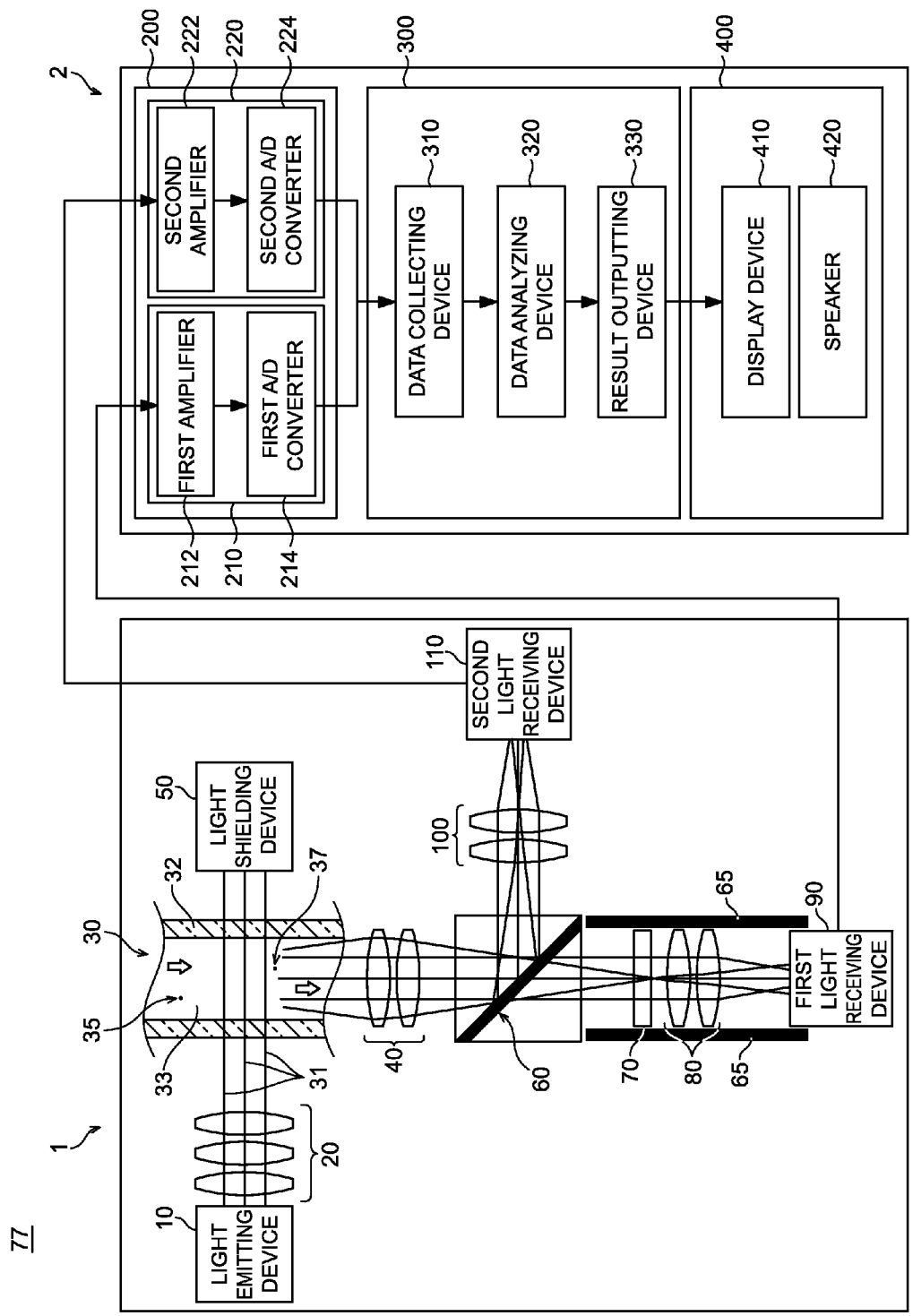
FIG. 1 is a schematic block diagram illustrating one embodiment of a viable particle counting apparatus.

FIG. 1 schematically illustrates a viable particle counting apparatus 77 of one embodiment The viable particle counting apparatus 77 includes a light detecting system 1 and an autofluorescence light counting system 2. The light detecting system 1 radiates a light to a target to detect a scattered light and an autofluorescence light from the target. The autofluorescence light counting system 2 counts the number of the autofluorescence lights based on signals output from the light detecting system 1. By these systems 1, 2, the counting apparatus 77 is capable of detecting and counting viable particles among targets in water. Incidentally, the viable particles that can be detected (counted) by the counting apparatus 77 are viable particles with, for example, a 0.1 μm to several 100 μm size, and concretely, are bacteria, yeast, mold, and the like. Further, the light radiated to the viable particles is a laser light in an ultraviolet region, and the autofluorescence light emitted from a substance (riboflavin, NAD(P)H (nicotinamide adenine dinucleotide (phosphate)), or the like) existing in a body (cell) of the viable particle and necessary for metabolism is detected as an index.

[Light Detecting System]

The light detecting system 1 includes, for example, a light emitting device 10, a radiation optical lens system 20, a device 30 which makes the target flow therein, a first condensing optical lens system 40, a light shielding device 50, a device 60 which reflects a scattered light, a light shielding device 65, a device 70 which selects the autofluorescence light of the viable particle, a second condensing optical lens system 80, a first light receiving device 90, a third condensing optical lens system 100, and a second light receiving device 110. By these constituent elements, the system 1 is capable of radiating the light to the target and detecting the scattered light and the autofluorescence light from the target.

More concretely, the counting of the viable particles by the counting apparatus 77 has, for example, the following features and progresses according to a predetermined procedure.

(1) Assuming that a liquid containing a target is flowing in a flow cell 30, the liquid containing the target flowing in the flow cell 30 is irradiated with a light with a specific wavelength. For example, a laser light with a single wavelength is radiated from the laser diode 10. Here, the target represents a viable particle, a non-viable particle, or the like. Further, the liquid represents, for example, water.

(2) The irradiation with the laser light in the above (1) results in the emission of lights due to an interaction of the laser light and the target or an interaction of the laser light and the liquid. Concretely, main emitted lights are a scattered light emitted due to reflection or the like by the viable particle, an autofluorescence light emitted by utilizing energy generated by the absorption of the laser light by the viable particle, a scattered light emitted due to reflection or the like by the non-viable particle, and a Raman-scattered light emitted as a result that the wavelength of the light incident on the liquid (molecule) is converted. Note that the wavelength of the radiated laser light is set so that a peak wavelength in a spectrum of the autofluorescence light becomes different from peak wavelengths of the scattered light and the Raman-scattered light.

(3) The wavelengths of the lights emitted in the above (2) are different from one another, and for example, the scattered light from the viable particle or the non-viable particle is about equal in wavelength to the laser light, while the lights such as the Raman-scattered light and the autofluorescence light are longer in wavelength than the laser light. Further, as for the wavelengths of the Raman-scattered light and the autofluorescence light, their wavelength distribution regions sometimes overlap with each other, and therefore, for example, a peak value (peak wavelength) of the wavelength distribution of the autofluorescence light is sometimes longer than a peak value (peak wavelength) of the wavelength distribution of the Raman-scattered light. By utilizing the fact that the peak wavelengths are made different between the autofluorescence light and the Raman-scattered light by the setting of the wavelength of the radiated laser light, it is possible to make an amount of the Raman-scattered light smaller than an amount of the autofluorescence light by using an optical separating device using a specific wavelength (cut-off wavelength) as a reference. For example, by using a long-pass filter using a specific wavelength as a reference or a band-pass filter, the Raman-scattered light is reduced and most of the autofluorescence light is transmitted.

(4) Based on the light transmitted in the above (3), that is, the autofluorescence light from the viable particle, it is determined whether or not the target contained in the liquid is the viable particle. Then, when it is determined in this determination that the target is the viable particle, the number thereof is counted. In this manner, the number of the viable particles is counted.

As described above, according to the counting apparatus 77 of this embodiment, it is possible to determine whether or not the viable particle exists in the liquid while reducing an influence of the Raman-scattered light caused by the liquid. This is because, by using the irradiating light that causes the Raman-scattered light by the liquid and the autofluorescence light to be different in peak wavelength, it is possible to optically reduce the Raman-scattered light and on the other hand to transmit the autofluorescence light from the viable particle. Consequently, it is possible to improve counting accuracy of the viable particles.

Figure 2:
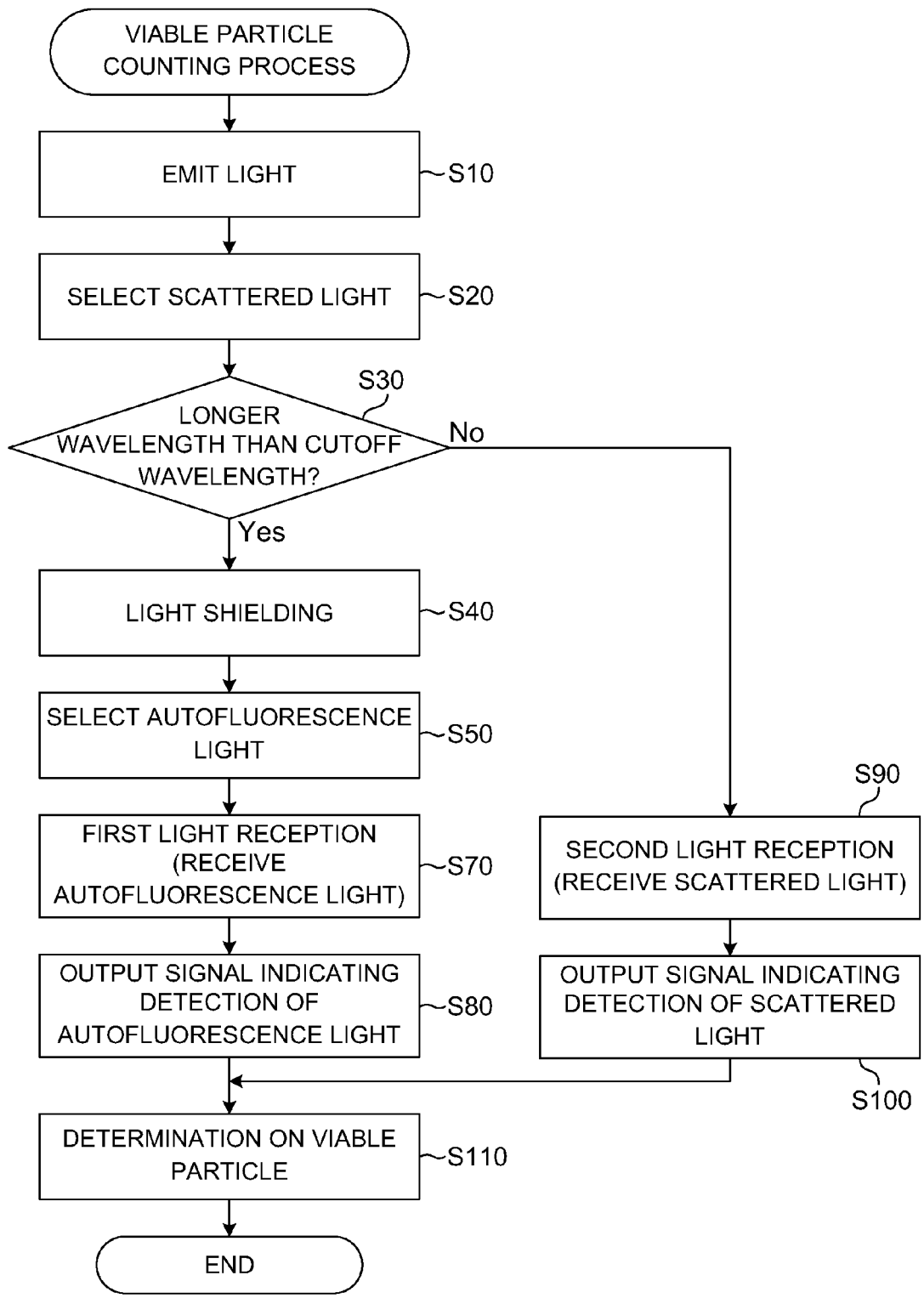
FIG. 2 is a flowchart illustrating a procedure example of a process of a viable particle counting method using the viable particle counting apparatus.

FIG. 2 is a flowchart illustrating a procedure example of a viable particle counting process using the counting apparatus 77. Hereinafter, the concrete procedure will be described in sequence.

Step S10: In the viable particle counting process, a step of radiating the laser light toward the liquid as a detection target is first executed by the light emitting device 10.

Step S20: A step of separating lights is executed by the device 60 which reflects the scattered light. The light separation of this step is performed based on whether or not lights obtained after Step S10 have a wavelength longer than the predetermined cutoff wavelength. Here, the lights obtained after Step S10 refer to the autofluorescence light and the scattered light of the viable particle and the Raman-scattered light by the liquid which are emitted as a result of the radiation of the laser light.

Step S30: A subsequent process is separated depending on whether or not the light having undergone Step S20 has a wavelength longer than the cutoff wavelength. Note that the wavelength longer than the cutoff wavelength refers to a wavelength of a transmitted light without being reflected by the device 60 which reflects the scattered light.

When the light having undergone Step S20 has a wavelength longer than the cutoff wavelength (Step S30: Yes), the counting process goes to Step S40. On the other hand, when this light has a wavelength shorter than the cutoff wavelength (Step S30: No), the counting process goes to Step S90.

Step S40: A step of preventing an external light from entering is executed by the light shielding device 65. This light shielding step is performed for the transmitted light (Step S30: Yes) having undergone Step S20 inside a light path up to the first light receiving device 90.

Step S50: A step of selecting a light having a longer wavelength than a predetermined cutoff wavelength from the transmitted lights (Step S30: Yes) is executed by the device 70 which selects the autofluorescence light.

Step S70: A step of receiving the light obtained after Step S50 is executed by the first light receiving device 90.

Step S80: Further, a step of outputting a signal based on the light received by the device 90 at Step S70 is executed by the device 90.

Step S90: Regarding the light having undergone Step S20 to be reflected by the device 60 (Step S30: No), a step of receiving the reflected light is executed by the second light receiving device 110.

Step S100: Further, a step of outputting a signal based on the light received by the device 110 at Step S90 is executed by the device 110.

Step S110: A determining step using the signals output at Step S80 and Step S100 is executed by the autofluorescence light counting system 2. Further, by this determining step, the detection of the viable particles and the counting thereof are finally executed.

By the viable particle counting method including a series of the processes from Step S10 to Step S110, it is possible to detect and count the viable particles in the liquid.

Hereinafter, the constituent elements included in the counting apparatus 77 and the procedures of the viable particle counting method will be concretely described.

[Light Emitting Device (Step S10)]

The light emitting device 10 includes, for example, a semi-conductor laser diode (including a semiconductor LED element. Hereinafter, referred to as a laser diode). By the laser diode 10, the laser light is oscillated and radiated to the liquid containing the viable particles. A wavelength of the laser light oscillated by the laser diode 10 is decided according to a substance existing in the cell of the viable particle and capable of emitting the autofluorescence light (hereinafter, referred to as an autofluorescent substance). Here, the autofluorescent substance has an excitation wavelength with which energy of the radiated light is easily absorbed to facilitate the excitation to the excited state. The excitation wavelength differs depending on the substance, and further, a wavelength of the autofluorescence light emitted at the time of the return to a ground state from the excited state also differs depending on the autofluorescent substance. The excitation wavelength of the autofluorescent substance and the wavelength of the autofluorescence light will be described, taking concrete examples.

[Excitation Wavelength and Autofluorescence Light Wavelength]

Figure 3:
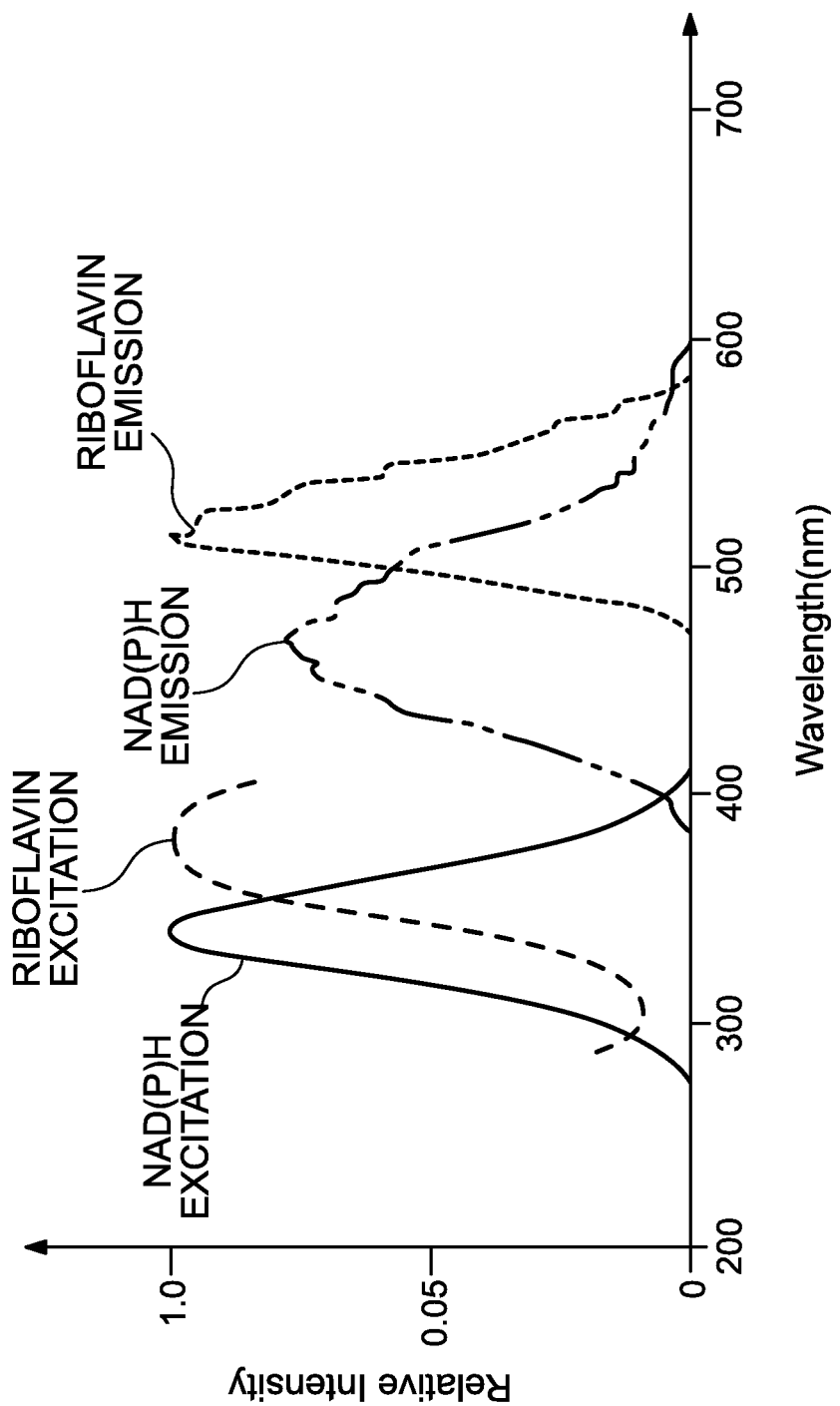
FIG. 3 is a chart illustrating excitation absorption spectrums of riboflavin and NAD(P)H being examples of an autofluorescent substance and spectrums of autofluorescence lights from the substances.

FIG. 3 illustrates examples of excitation absorption spectrums of the autofluorescent substances and spectrums of the autofluorescence lights from the substances.

As illustrated in FIG. 3, these distributions represent an excitation wavelength spectrum of NAD(P)H, an excitation wavelength spectrum of riboflavin, a spectrum of an autofluorescence light from NAD(P)H, and a spectrum of an autofluorescence light from riboflavin. For example, the excitation wavelength spectrum of NAD(P)H presents a distribution having a peak at an about 340 nm wavelength. Further, the excitation wavelength spectrum of riboflavin presents a distribution having a peak at an about 375 nm wavelength. This indicates that the radiation of a laser light having a 375 nm to 420 nm wavelength to the viable particle facilitates the excitation of riboflavin.

Thus, the wavelength of the laser light oscillated from the laser diode 10 is decided according to the excitation wavelength of NA(P)H or riboflavin existing in the cells of the viable particles. Consequently, it is possible to cause the emission of many autofluorescence lights from the viable particles. In this embodiment, it is assumed that the laser light having a 405 nm wavelength is oscillated from the laser diode 10. The radiation of this laser light having the 405 nm wavelength causes the emission of the autofluorescence lights by the riboflavin from the viable particles.

[Radiation Optical Lens System]

The radiation optical lens system 20 includes, for example, a plurality of kinds of optical lenses. For example, it includes a collimator lens, a biconvex lens, a cylindrical lens, and so on. This lens system 20 adjusts the laser light oscillated from the laser diode 10 to parallel rays to radiate them to the target.

[Device which Makes Target Flow Therein]

The device 30 which makes the target flow therein (flow cell 30) is formed by, for example, a tube part 32 which is a hollow quadratic prism made of synthetic quartz, sapphire, or the like. This device 30 has a structure in which a liquid 33 containing the target (viable particles 35 or non-viable particles 37) flows from top to bottom. The laser light 31 oscillated from the laser diode 10 is radiated to a hollow area of the tube part 32 in which the liquid flows, so that a detection area is formed there.

In this detection area, when the laser light 31 is radiated to water (water molecules) of the liquid 33 flowing in the flow cell 30 and the target (the viable particle 35 or the non-viable particle 37), they interact with each other.

The scattered light from the viable particle 35 is also emitted with a 405 nm wavelength. This is because the wavelength of the laser light 31 incident on the viable particle 35 is 405 nm. Further, as illustrated in FIG. 3, when the laser light 31 is absorbed by riboflavin in the cell of the viable particle 35, the wavelength distribution of the autofluorescence light by the riboflavin emitted from the viable particle 35 has a peak at about 520 nm. Here, the scattered light or the autofluorescence light emitted from the viable particle 35 is emitted to a surrounding area.

Further, the wavelength distribution of the scattered light by the laser light 31 incident on the non-viable particle 37 is the same as that of the scattered light emitted from the viable particle 35.

As described above, the scattered light from the viable particle 35 or the non-viable particle 37, or the autofluorescence light from the viable particle 35 is emitted. This is because the viable particle 35 or the non-viable particle 37 interacts with the laser light 31. Then, these lights are detected by the light receiving devices. Further, before reaching the light receiving devices, these lights pass through the plural condensing lens systems and the optical devices which select a light according to a wavelength. Incidentally, the intensity of the scattered light, that is, a light amount of the scattered light depends on the size of the viable particle 35 or the non-viable particle 37, and the larger the size, the larger the light amount.

Here, the intensity of the autofluorescence light from the viable particle 35 depends on an amount of the riboflavin in the cell of the viable particle 35. It also depends on a light amount (intensity) of the laser light 31, and by increasing laser power and thus radiating the laser light 31 in large quantity to the flow cell 30, the scattered light from the viable particle 35 or the non-viable particle 37 and the autofluorescence light from the viable particle 35 also increase. However, a light other than the scattered light from the viable particle 35 or the non-viable particle 37 and the autofluorescence light from the viable particle 35 also increases, concretely, a light (Raman-scattered light) due to the interaction between the laser light 31 and the water 33 (Raman scattering) also increases. Next, the Raman-scattered light by the water will be concretely described.

[Raman Scattering by Water]

Figure 4:
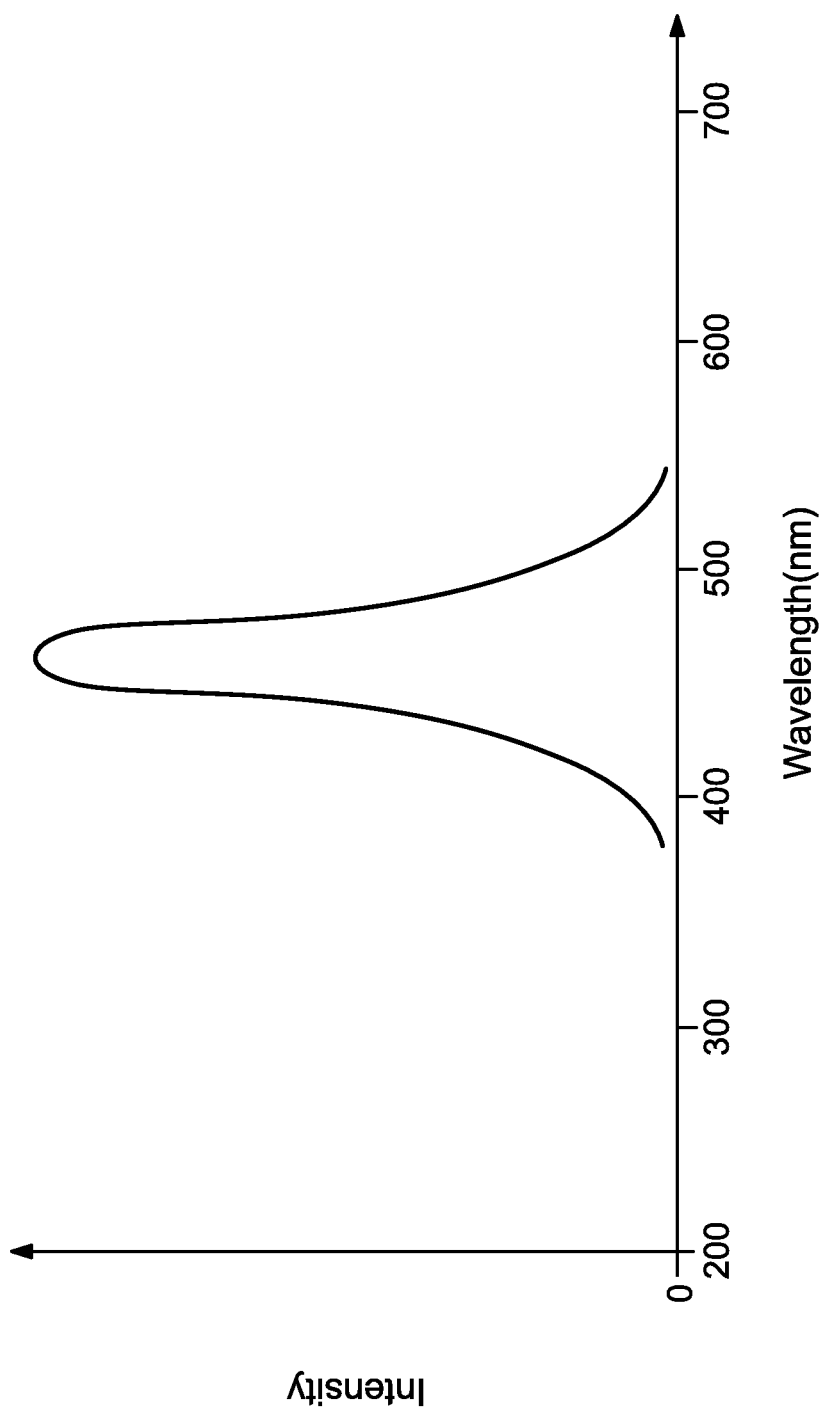
FIG. 4 is a schematic chart of a spectrum of a Raman-scattered light by water at the time of irradiation with a light with a 405 nm wavelength.

FIG. 4 is a chart illustrating an example of a spectrum of the Raman-scattered light by the water when the light having the 405 nm wavelength is radiated. As illustrated in FIG. 4, when the laser light 31 having the 405 nm wavelength is radiated to the water, the Raman-scattered light whose wavelength distribution has a peak at an about 465 nm wavelength is emitted due to the interaction between the water and the laser light 31.

[Light Shielding Device]

The light shielding device 50 is formed by, for example, a laser trap. For example, even when the laser light 31 is oscillated from the laser diode 10, part thereof passes without undergoing the interaction in the flow cell 30. This laser light 31 which has passed is shut off by the laser trap 50. By this light shielding, the laser light 31 which has passed is prevented from being reflected at various places, and is inhibited from causing the generation of the scattered light by the viable particles and becoming noise in the detection of the autofluorescence light.

[First Condensing Optical Lens System]

The first condensing optical lens system 40 includes, for example, a plurality of optical lenses. The first condensing optical lens system 40 is installed at an about 90 degree angle position relative to a travelling direction (optical axis) of the laser light 31. By the first condensing optical lens system 40, the scattered light from the viable particle 35 or the non-viable particle 37 and the autofluorescence light from the viable particle 35 in the flow cell 30 are gathered. Incidentally, in order to gather as many side scattered lights and autofluorescence lights as possible from the viable particles 35, a lens aperture is preferably larger. The lens aperture is decided according to a position (distance) at which a detecting apparatus which detects the scattered light and the autofluorescence light from the viable particle 35 is provided.

[Device which Reflects Scattered Light (Step S20)]

The device 60 which reflects the scattered light is formed by, for example, a dichroic mirror. The dichroic mirror 60 of this embodiment transmits a light having a wavelength longer than 410 nm and reflects a light having a wavelength shorter than 410 nm. A specific wavelength as a reference for such separation based on the light wavelength will be called a cutoff wavelength. Here, the wavelength of the scattered light from the viable particle 35 or the non-viable particle 37 scattered by the 405 nm laser light 31 in the flow cell 30 is mainly 405 nm. Therefore, the dichroic mirror 60 is capable of reflecting the scattered light from the viable particle 35 or the non-viable particle 37. Further, the reflected scattered light from the viable particle 35 or the non-viable particle 37 form an image on the second light receiving device 110. Incidentally, this image formation is caused by the third condensing optical lens system 100 gathering the lights.

On the other hand, regarding the autofluorescence light emitted from the viable particle 35 flowing in the flow cell 30, its wavelength distribution has a peak at about 520 nm as illustrated in FIG. 3. Therefore, this autofluorescence light is mostly transmitted without being reflected by the dichroic mirror 60. Further, the wavelength distribution of the Raman-scattered light by the water has a peak at about 465 nm and is mostly occupied by wavelengths longer than the 410 nm cutoff wavelength as illustrated in FIG. 4. Therefore, most of the Raman-scattered light except part thereof is transmitted by the dichroic mirror 60. Then, the transmitted autofluorescence light and Raman-scattered light by the water next progress to the device 70 which selects the autofluorescence light.

Note that the cutoff wavelength serving as the reference of the dichroic mirror 60 is not limited to 410 nm and may be such a wavelength that the scattered light from the viable particle 35 or the non-viable particle 37 scattered by the laser light 31 is reflected and the autofluorescence light from the viable particle 35 is transmitted.

[Device which Selects Autofluorescence Light (Step S50)]

The device 70 which selects the autofluorescence light is formed by, for example, an optical filter. In this embodiment, a long-pass filter 70 which transmits a light having a wavelength longer than a 490 nm wavelength (cutoff wavelength) is provided.

On the other hand, about 90% of the Raman-scattered light by the water can be cut off by the device 70. This is because most of the Raman-scattered light except part thereof has a wavelength shorter than the 490 nm cutoff wavelength as illustrated in FIG. 4.

[Change of Intensity Distribution of Raman-Scattered Light by Water Before it Enters Long-Pass Filter]

Figure 5:
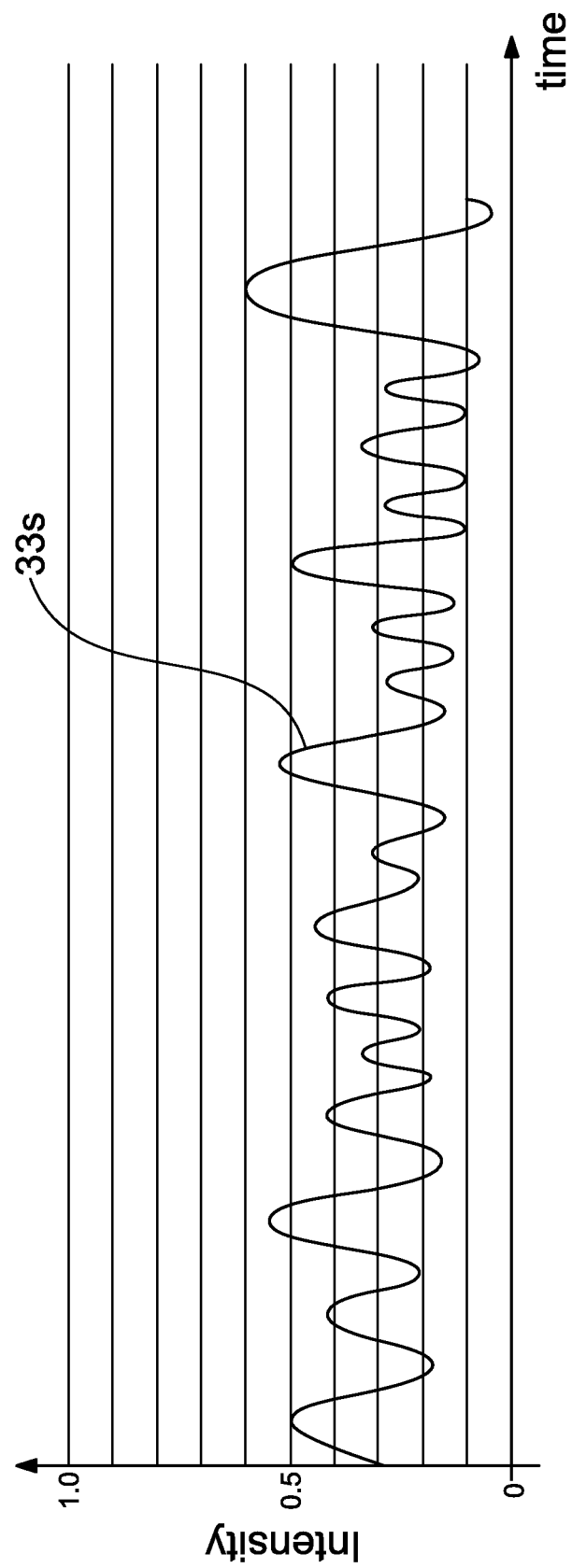
FIG. 5 is a chart illustrating an example of how intensity distribution of the Raman-scattered light by the water before it enters an optical filter changes with time.
Figure 6:
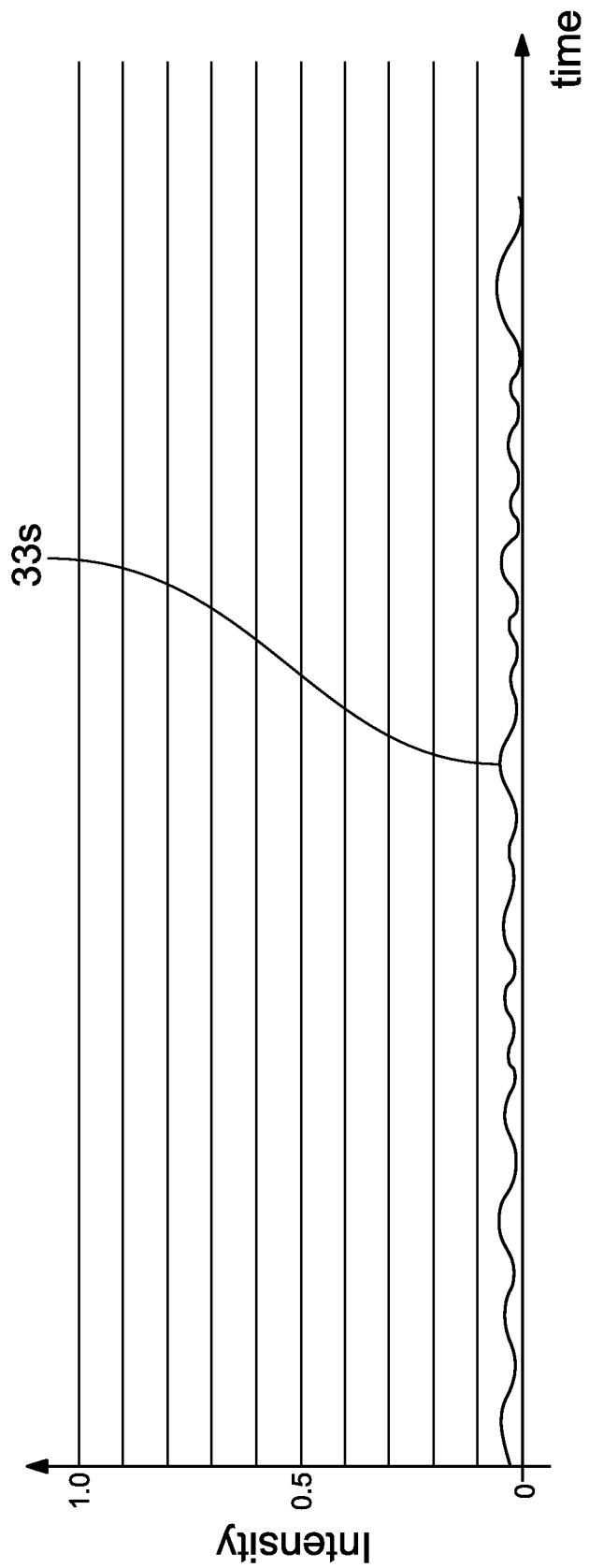
FIG. 6 is a chart illustrating an example of how intensity distribution of the Raman-scattered light by the water after it is transmitted by the optical filter changes with time.

FIG. 5 illustrates an example of intensity distribution of the Raman-scattered light by the water in accordance with time before it enters the long-pass filter. On the other hand, FIG. 6 illustrates an example of intensity distribution of the Raman-scattered light by the water in accordance with time after it is transmitted by the long-pass filter. FIG. 5 and FIG. 6 show that the intensity distribution of the Raman-scattered light 33s by the water is changed by the long-pass filter.

[Intensity Distribution of Raman-Scattered Light by Water Before it Enters Long-Pass Filter]

In FIG. 5, the horizontal axis represents time and the vertical axis represents intensity of the light expressed in an arbitrary unit. The Raman-scattered light 33s by the water presents a distribution where a random increase/decrease is repeated. For example, it is shown that the Raman-scattered light 33s by the water sometimes presents a distribution where a peak of its intensity is 0.5 and sometimes presents a distribution where the peak is 0.3, and an amount of the entering Raman-scattered light 33s by the water is sometimes large and in some other times, is small. This indicates that the Raman-scattered light 33s enters at random irrespective of the time.

[Intensity Distribution of Raman-Scattered Light by Water after it is Transmitted by Long-Pass Filter]

Further, in FIG. 6, the horizontal axis represents time and the vertical axis represents intensity of the light expressed in an arbitrary unit. It is shown that the intensity of the Raman-scattered light 33s by the water after it is transmitted by the long-pass filter 70 changes to about $1/10$ of that in the intensity distribution of the Raman-scattered light 33s by the water illustrated in FIG. 5.

As described above, according to the apparatus 77 of this embodiment, it is possible to further improve counting accuracy of the viable particles. This is made possible by using the autofluorescence light from riboflavin in the cell of the viable particle in the water as an index. For this purpose, the 405 nm laser light is first radiated in order to easily excite an energy state of the riboflavin. Thereafter, the autofluorescence light whose peak wavelength is about 520 nm is emitted from the riboflavin and the Raman-scattered light whose peak wavelength is about 465 nm is emitted from the water. Therefore, by setting the cutoff wavelength serving as the reference of the long-pass filter 70 to 490 nm, it is possible to efficiently separate the autofluorescence light and the Raman-scattered light.

Next, not only the Raman-scattered light 33s by the water but also a light Lt transmitted by the dichroic mirror will be described. The light Lt includes the Raman-scattered light 33s by the water and the autofluorescence light 35e emitted from the viable particle 35.

[Change of Intensity Distribution of Light Before it Enters Long-Pass Filter]

Figure 7:
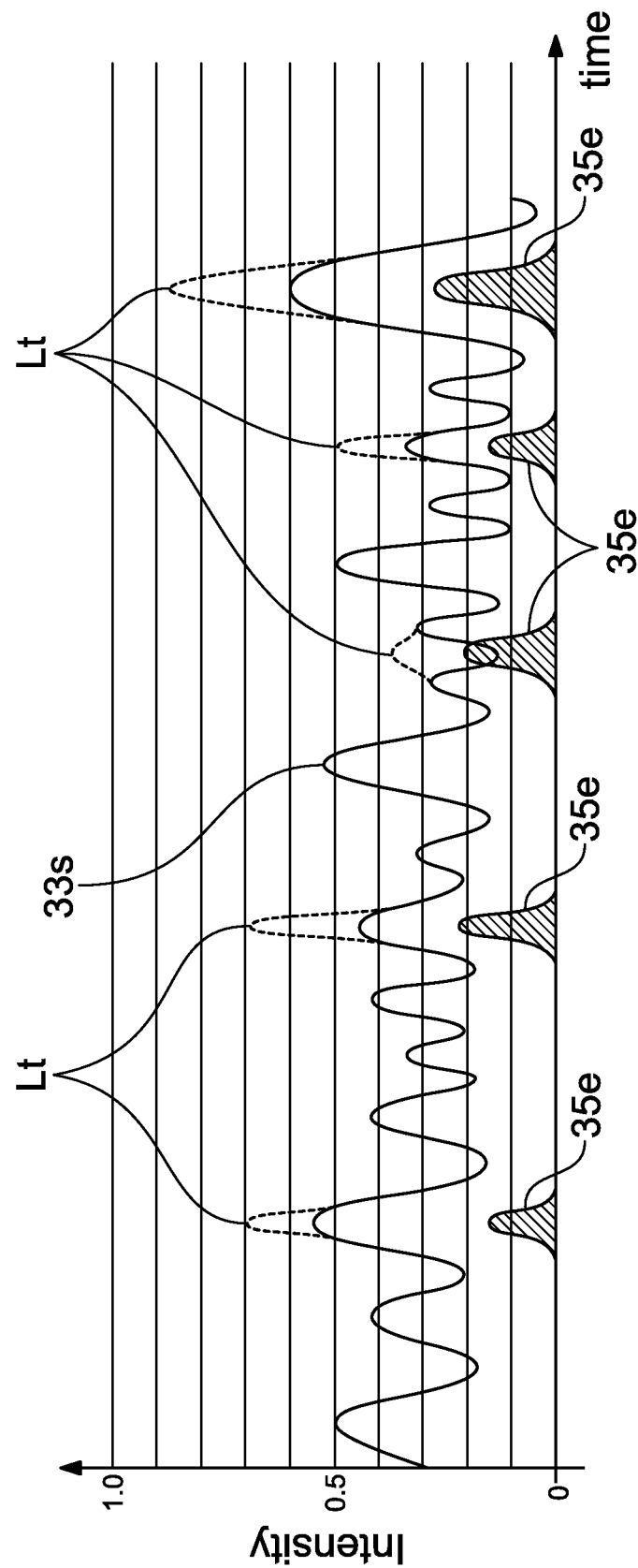
FIG. 7 is a chart illustrating an example of how intensity distributions of all lights before they enter the optical filter change with time.
Figure 8:
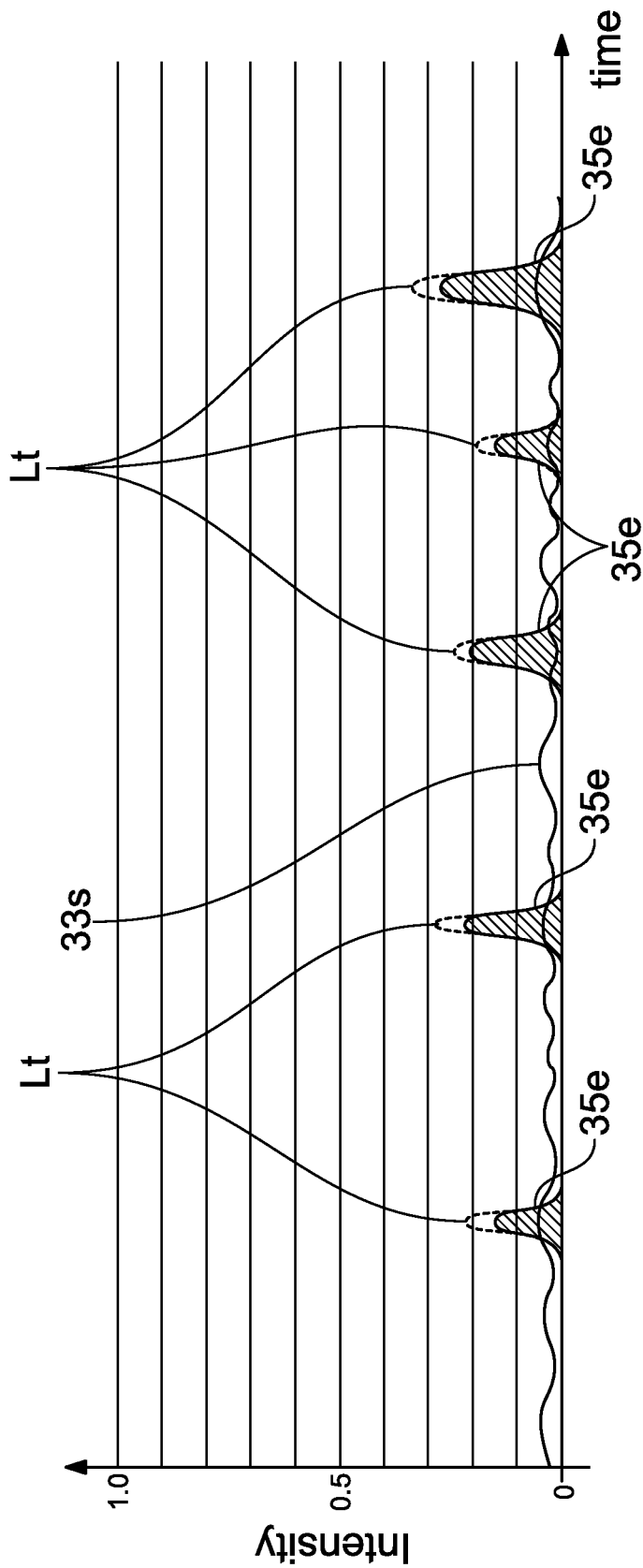
FIG. 8 is a chart illustrating an example of how intensity distributions of all lights after they are transmitted by the optical filter change with time.

FIG. 7 illustrates an example of how intensity distributions of all the lights before they enter the optical filter change with time. On the other hand, FIG. 8 illustrates an example of how intensity distributions of all the lights after they are transmitted by the optical filter change with time. From FIG. 7 and FIG. 8, it is seen that the intensity distribution of the total light Lt transmitted by the dichroic mirror 60 is separated by the long-pass filter 70.

[Intensity Distribution of Light Before it Enters Long-Pass Filter]

In FIG. 7, the horizontal axis represents time and the vertical axis represents relative intensity of the light. The distribution of the light entering the long-pass filter 70 is the distribution of the light Lt. Concretely, the light Lt is the combination (sum) of the distribution of the Raman-scattered light 33s by the water and the distribution of the autofluorescence light 35e. For example, it is assumed that the Raman-scattered light 33s by the water in whose light amount distribution a relative intensity peak is 0.5 and the autofluorescence light 35e in whose light amount distribution a relative intensity peak is 0.2 enter during a time period Δt from a given time instant. In this case, the light Lt whose amount is the sum of these light amounts enters during the time period Δt, and the relative intensity distribution of the light Lt is a distribution where 0.7 is a peak.

[Intensity Distribution of Light after it is Transmitted by Long-Pass Filter]

Further, FIG. 8 illustrates the time-variable distribution of the total light Lt transmitted by the long-pass filter. Concretely, it illustrates a combined distribution of the time-variable intensity distribution of the light amount of the Raman-scattered light 33s by the water which becomes about 10% of that at the time of the entering and the time-variable intensity distribution of the light amount of the autofluorescence light 35e which does not change from that at the time of the entering. For example, it is assumed that the Raman-scattered light 33s by the water in whose light amount distribution the peak of the relative intensity is 0.05 and the autofluorescence light 35e in whose light amount distribution the peak of the relative intensity is 0.2 are transmitted during a time period Δt from a given time instant. In this case, the light Lt whose amount is the sum of these light amounts is transmitted during this time period Δt, and a relative intensity distribution of the light Lt is a distribution where the peak is 0.25.

Note that, as the wavelength reference for the light separation by the device 70 which selects the autofluorescence light, a wavelength is selected so that the intensity of the Raman-scattered light 33s by the water becomes less than that of the autofluorescence light 35e emitted from the viable particle 35. Concretely, the cutoff wavelength is not limited to 490 nm and may be a wavelength having any value between 450 nm and 520 nm, preferably between 450 nm and 490 nm. Further, the long-pass filter that transmits wavelengths longer than 490 nm is not restrictive, and a band-pass filter that transmits lights in a 490 nm to 600 nm wavelength band may be provided.

Here, as the device 70, the long-pass filter which uses the aforesaid cutoff wavelength (for example, 490 nm) as the reference is provided. This is because the autofluorescence light 35e from the riboflavin in the cell of the viable particle 35 is used as the index. On the other hand, when NAD(P)H in the cell of the viable particle 35 is used as an index, a different type of the device 70 which selects the autofluorescence light may be provided. For example, a long-pass filter whose cutoff wavelength is any wavelength (for example, 450 nm) between 410 nm and 470 nm and which transmits lights having wavelengths longer than the cutoff wavelength or a band-pass filter which transmits lights in a 450 nm to 600 nm wavelength band as a cutoff wavelength may be provided. This is because, when the laser light 31 with about 350 nm is radiated, the Raman-scattered light 33s by the water presents a distribution having a peak at 400 nm. Further, this is because, by the long-pass filter whose reference is 450 nm, it is possible to cut off most of the Raman-scattered light 33s by the water similarly to the case where the detection of the autofluorescence light 35e from the riboflavin is used as an index.

[Second Condensing Optical Lens System: Refer to FIG. 1]

The second condensing optical lens system 80 includes, for example, a plurality of optical lenses.

The second condensing optical lens system 80 is installed on a travelling direction (optical axis) of the light transmitted by the long-pass filter 70. By this second condensing optical lens system 80, the autofluorescence light 35e and the Raman-scattered light 33s by the water which are transmitted by the long-pass filter 70 are gathered, and an image is formed on a plane of incidence of the first light receiving device 90.

[First Light Receiving Device (Step S70, Step S80)]

The first light receiving device 90 is formed by, for example, a semiconductor light receiving element (photodiode: PD) or a photo multiplier tube (PMT) higher in sensitivity than the photodiode. The photodiode or the photo multiplier tube (hereinafter referred to as a photo multiplier) converts a received light to a current to output the current according to an amount of the received light. Note that intensity of the output current changes depending on the amount of the received light, and the larger the amount of the received light, the larger the intensity of the current. Note that an electric signal output from the photo multiplier 90 is next input to the autofluorescence light counting system 2.

[Light Shielding Device 65 (Step S40)]

The light shielding device 65 is formed by a cylindrical structure surrounding a light path from a transmission side of the dichroic mirror 60 to the photo multiplier 90. By this light shielding device 65, it is possible to prevent lights except the light (autofluorescence light 35e) transmitted by the dichroic mirror 60 from entering the photo multiplier 90. For example, it is possible to shut off the Raman-scattered light 33s and the scattered lights 35s, 37s from the target so that these lights do not enter this light path by being reflected in the light detecting system 1. A light shielding device, not illustrated, may similarly be provided in a light path from the opposite side of the dichroic mirror 60 to the second light receiving device 110, and so on.

[Third Condensing Optical Lens System]

The third condensing optical lens system 100 includes, for example, a plurality of optical lenses. The third condensing optical lens system 100 is installed on a travelling direction (optical axis) of the light reflected by the dichroic mirror 60.

[Second Light Receiving Device (Step S90, Step S100)]

The second light receiving device 110 is formed by, for example, a photodiode or a photo multiplier. Here, the light entering the device 110 is a light with a wavelength shorter than 410 nm reflected by the dichroic mirror 60, and concretely, the scattered light scattered by the viable particle 35 or the non-viable particle 37 flowing in the flow cell 30. The scattered light by the viable particle 35 or the non-viable particle 37 can be sufficiently detected even by an inexpensive photodiode instead of a photo multiplier. This is because the scattered light by the viable particle 35 or the non-viable particle 37 has a larger light amount than that of the autofluorescence light 35e emitted from the viable particle 35. In this embodiment, the photodiode 110 is provided, which receives the scattered light by the viable particle 35 or the non-viable particle 37 reflected by the dichroic mirror 60. The light received by the photodiode 110 is converted to an electric signal according to its light amount, and the electric signal is output from the photodiode 110. The output signal from the photodiode 110 is next input to the autofluorescence light counting system 2.

[Autofluorescence Light Counting System (Step S110): Refer to FIG. 1]

Figure 9:
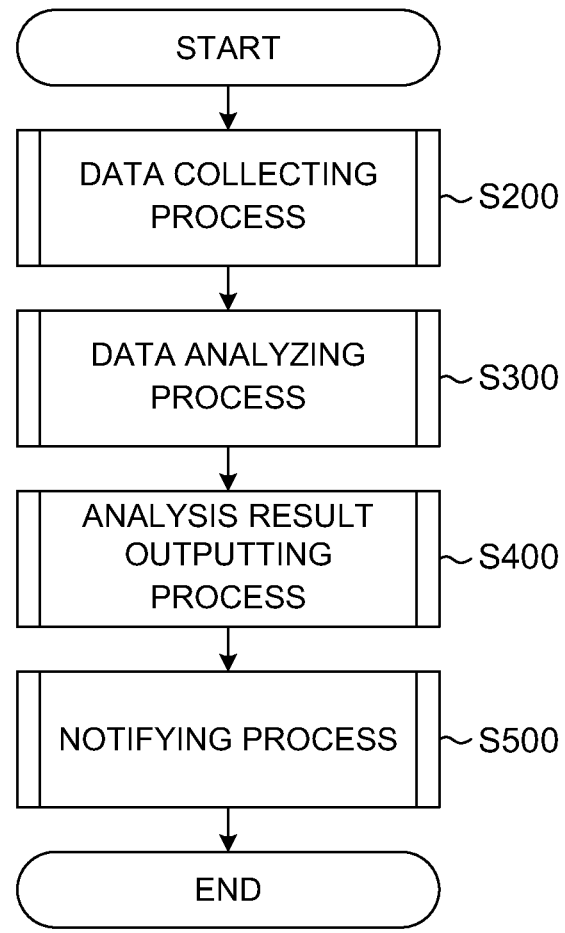
FIG. 9 is a flowchart illustrating a procedure example of an autofluorescence light counting process.

The autofluorescence light counting system 2 includes, for example, a detection signal processing part 200, a data processing part 300, and a notifying part 400. Further, FIG. 9 is a flowchart illustrating a procedure example of an autofluorescence light counting process.

Step S200 (Data collecting process): The detection signal processing part 200 first receives, for example, the output signals from the light detecting system 1, that is, the output signal from the first light receiving device (photo multiplier) 90 and the output signal from the second light receiving device (photodiode) 110. Next, the detection signal processing part 200 amplifies the received signals. Finally, the detection signal processing part 200 performs processing of AD-converting the analog signals to digital signals, and so on.

Step S300 (data analyzing process): For example, the data processing part 300 receives and stores an autofluorescence light signal (signal A) and a scattered light signal (signal B) obtained by the AD conversion processing by the detection signal processing part 200.

Step S400 (analysis result outputting process): Based on the stored signal A and signal B, the data processing part 300 further determines whether or not the signal ascribable to the viable particle 35 in the liquid, that is, the signal ascribable to the autofluorescence light 35e is included. Finally, the data processing part 300 performs processing of outputting the determination result, and so on.

Step S500 (notifying process): For example, the notifying part 400 notifies the result determined by the data processing part 300 to the outside of the apparatus or outputs a notification signal to the outside of the apparatus.

Hereinafter, the constituent elements of the autofluorescence light counting system 2 illustrated in FIG. 1 and their processes will be concretely described.

[Detection Signal Processing Part]

For example, the detection signal processing part 200 includes a device 210 which processes a signal indicating that the autofluorescence light is received and a device 220 which processes a signal indicating that the scattered light is received. The device 210 includes, for example, a first amplifier 212 and a first analog/digital converter 214. The device 220 includes, for example, a second amplifier 222 and a second analog/digital converter 224.

[Data Collecting Process]

Figure 10:
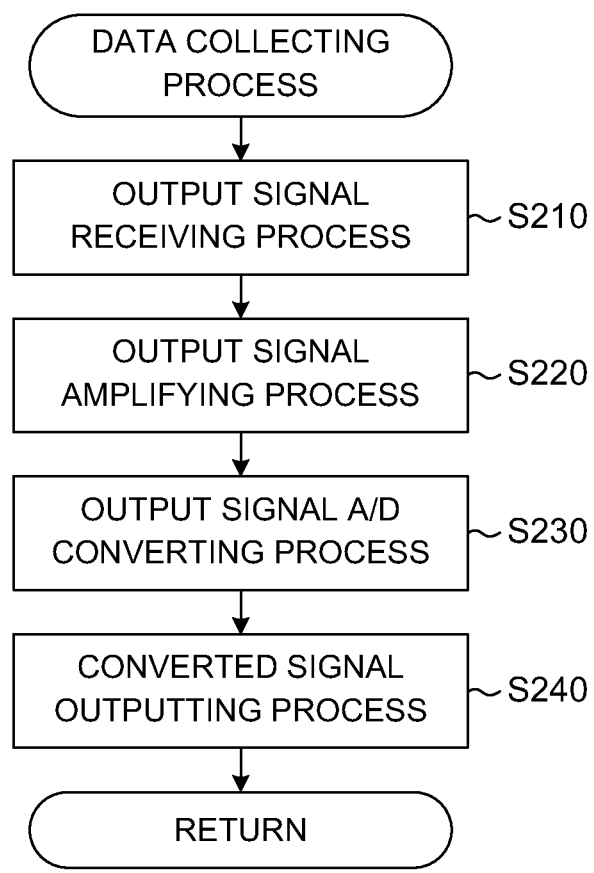
FIG. 10 is a flowchart illustrating a procedure example of a data collecting process.

FIG. 10 is a flowchart illustrating a procedure example of the data collecting process.

First, when the device 210 which processes the signal indicating that the autofluorescence light is received receives the output signal from the first light receiving device (photo multiplier) 90 (output signal receiving process Step S210), the first amplifier 212 amplifies the output signal output from the photo multiplier 90 (output signal amplifying process Step S220). Then, the first analog/digital converter 214 converts the analog signal amplified by the first amplifier 212 to the digital signal (signal A) (output signal A/D converting process Step S230).

Similarly, when the device 220 which processes the signal indicating that the scattered light is received receives the output signal from the second light receiving device (photodiode) 110 (output signal receiving process Step S210), the second amplifier 222 amplifies the output signal output from the photodiode 110 (output signal amplifying process Step S220). Then, the second analog/digital converter 224 converts the analog signal amplified by the second amplifier 222 to the digital signal (signal B) (output signal A/D converting process Step S230).

Thereafter, the signal A and the signal B converted to the digital signals are output from the device 210 and the device 220 (converted signal outputting process Step S240). The output signal A and signal B are next input to the data processing part 300.

[Data Processing Part]

The data processing part 300 includes, for example, a data collecting device 310, a data analyzing device 320, and a result outputting device 330. Further, the data collecting device 310 includes, for example, a memory (RAM) 310 which stores data.

[Data Analyzing Process]

Figure 11:
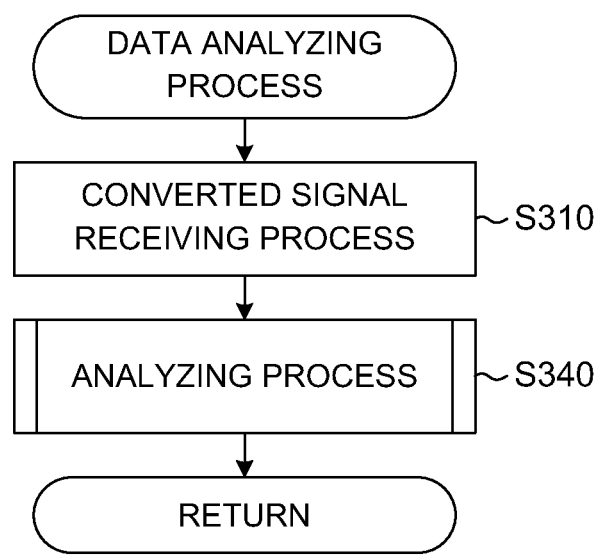
FIG. 11 is a flowchart illustrating a procedure example of a data analyzing process.

FIG. 11 is a flowchart illustrating a procedure example of the data analyzing process.

First, the data processing part 300 receives the signal A and the signal B output from the device 210 and the device 220 (converted signal receiving process Step S310). The received signal A and signal B are stored in a memory area of the memory 310 as they are.

When the storage of the signal A and the signal B to the memory 310 is finished, an analyzing process (analyzing process Step S340) is next performed by using these signal A and signal B.

[Data Analyzing Device (Determining Device, Signal Outputting Device)]

The data analyzing device 320 includes, for example, a calculating circuit (for example, CPU 322) which analyzes the data (the signal A and the signal B) stored in the memory 310 and a memory 324 (ROM) storing the calculation contents (program, threshold value data) and so on.

[Analyzing Process (Determining Step, Signal Outputting Step)]

Figure 12:
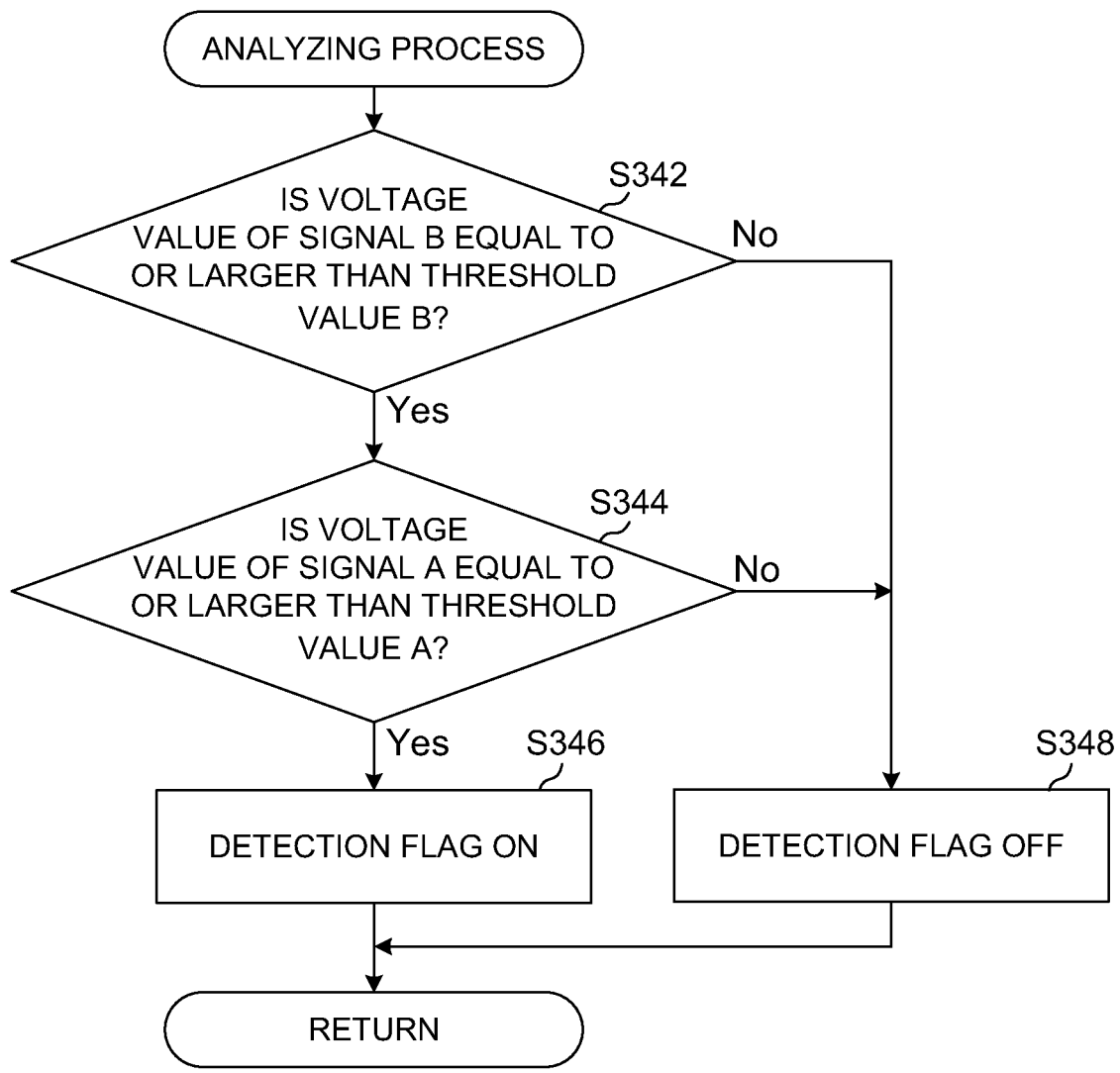
FIG. 12 is a flowchart illustrating a procedure example of an analyzing process.

FIG. 12 is a flowchart illustrating a procedure example of the analyzing process.

Step S342: The CPU 322 compares the signal B stored in the memory 310 with the threshold value data (voltage value) stored in advance in the memory 324. Concretely, it is determined whether or not a voltage value of the stored signal B is equal to or larger than a threshold value B (VthB).

When, as a result of this determination, it is determined that the voltage value of the signal B is equal to or larger than the threshold value B (Step S342: Yes), this indicates that the scattered light from the viable particle 35 or the non-viable particle 37 has entered the photodiode 110 and is detected. In this case, the analyzing process next goes to Step S344. Here, a process of setting a scattered light detection flag indicating that the scattered light from the viable particle 35 or the non-viable particle 37 is detected to ON may be performed.

On the other hand, when, as a result of this determination, it is determined that the voltage value of the signal B is less than the threshold value B (Step S342: No), the analyzing process next goes to Step S348.

Step S344: The CPU 322 compares the signal A stored in the memory 310 with the threshold value data (voltage value) stored in advance in the memory 324. Concretely, it is determined whether or not a voltage value of the stored signal A is equal to or larger than a threshold value A (VthA).

When, as a result of this determination, it is determined that the voltage value of the signal A is equal to or larger than the threshold value A (Step S344: Yes), this indicates that the autofluorescence light 35e emitted from the viable particle 35 has entered the photo multiplier 90 and is detected. In this case, the analyzing process next goes to Step S346.

On the other hand, when, as a result of this determination, it is determined that the voltage value of the signal A is less than the threshold value A (Step S344: No), the analyzing process next goes to Step S348.

Step S346: A process of setting a detection flag indicating that the autofluorescence light 35e is detected to ON is performed. Incidentally, the detection flag (ON) is next transmitted as a flag signal to the result outputting device 330.

Step S348: A process of setting the detection flag to OFF is performed. This flag indicates that the autofluorescence light 35e is not detected. Here, when the aforesaid scattered light detection flag is ON and the detection flag is OFF, a process of setting a non-viable detection flag indicating that the non-viable particle 37 which is not the viable particle 35 is detected to ON may be performed. Incidentally, this detection flag (OFF) is next transmitted as a flag signal to the result outputting device 330. Further, the non-viable detection flag may be also transmitted.

The above-described analyzing process will be concretely described by using charts of the signal A and the signal B corresponding to the output signals output from the respective light receiving devices.

[Examples of Output Signals from First Light Receiving Device and Second Light Receiving Device]

Figure 13:
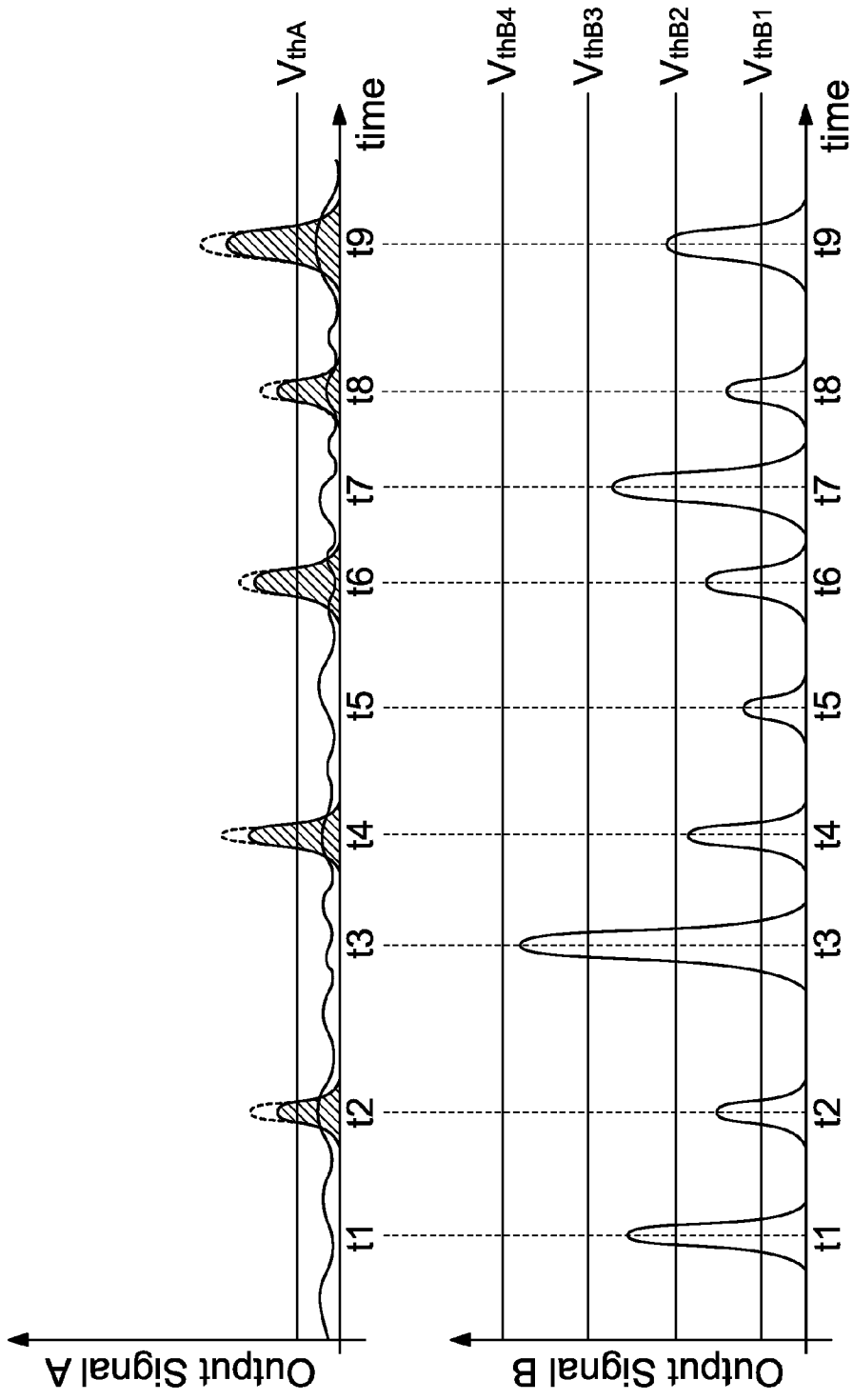
FIG. 13 is a chart illustrating examples of output signals from a first light receiving device and a second light receiving device.

FIG. 13 is a chart illustrating examples of the output signals from the first light receiving device 90 and the second light receiving device 110.

The signal on the upper side in FIG. 13 represents a time-variable distribution of the signal A corresponding to the detection signal output from the photo multiplier 90. The signal on the lower side in FIG. 13 represents a time-variable distribution of the signal B corresponding to the detection signal output from the photodiode 110. Here, it is assumed that the distributions of the signal A and the signal B illustrated on the upper and lower sides in FIG. 13 are distributions in which the timing of the time lapse of the both is adjusted. Further, regarding the time on the horizontal axis, it is shown that the time passes in order of times t1, t2, t3, . . . .

For example, if the voltage value of the signal B larger than the threshold value B (VthB (in FIG. 13, VthB1) is input to the data processing part 300 at the time t1, the CPU 322 determines that the voltage value of the signal B is equal to or larger than the threshold value B (Step S342: Yes). That is, this indicates that the scattered light from the viable particle 35 or the non-viable particle 37 enters the photodiode 110 and is detected at t1.

Then, the CPU 322 compares the threshold value A (VthA) stored in advance in the memory 324 with the voltage value of the signal A (Step S344). Since the signal A at the time t1 is not a signal having a larger value than the threshold value A (Step S344: No), the signal B at the time t1 indicates the scattered light from the non-viable particle 37, and the detection flag is set to OFF (Step S348).

Next, at the time t2, the CPU 322 determines that the voltage value of the signal B is equal to or larger than the threshold value B (Step S342: Yes).

Then, the CPU 322 compares the threshold value A (VthA) with the voltage value of the signal A (Step S344), and as a result, the CPU 322 determines that the voltage value of the signal A is equal to or larger than the threshold value A (Step S344: Yes). Therefore, the signal A and the signal B at the time t2 indicate the autofluorescence light 35e and the scattered light from the viable particle 35, and the detection flag is set to ON (Step S346).

In the above-described manner, the determination result on whether or not the viable particle 35 exists is obtained in real time. Here, the intensities of the signal A and the signal B depend on amounts of the lights entering the photo multiplier 90 and the photodiode 110, and the intensity of the scattered light depends on the size of the viable particle 35 or the non-viable particle 37. Therefore, not only the presence/absence of the viable particle 35 is detected but also the size of the viable particle 35 or the non-viable particle 37 can be measured based on the intensities of the signal A and the signal B.

As described above, according to the apparatus 77 of this embodiment, it is possible to determine whether or not the target contained in the liquid is the viable particle based on the mutual relation with the scattered light from the target. This is because the transmission of the Raman-scattered light is reduced and on the other hand the autofluorescence light from the viable particle is transmitted. For example, when the scattered light and the transmitted light exist, it can be determined that the target is the viable particle. Further, when only the scattered light exists, it can be determined that the target is the non-viable particle but not the viable particle. Further, when the transmitted light exists, it can be determined that this light is the Raman-scattered light caused by water. Consequently, it is possible to further improve counting accuracy of the viable particles. Further, according to an installation condition, it is possible to select the use of the optical separator such as the dichroic mirror, the long-pass filter, the band-pass filter, or the short-pass filter.

Further, by providing the predetermined threshold value for the scattered light of the target, it is possible to determine that the signal having a larger intensity than the threshold value indicates the scattered light of the target.

Here, it is assumed that a plurality of the threshold values B (VthB1, VthB2, VthB3, VthB4, . . . ) corresponding to the sizes (0.1 µm to 0.3 µm, 0.3 µm to 0.5 µm, 0.5 µm to 1.0 µm, . . . ) of the viable particles 35 are stored in the memory 324 in advance. For example, since the signal B at the time t2 has the intensity larger than VthB 1 and smaller than VthB2, the size of the viable particle 35 is measured as 0.1 µm to 0.3 µm. Incidentally, the plural threshold values B corresponding to the sizes of the viable particles 35 (0.1 µm or larger, 0.2 µm or larger, . . . ) may be stored, and these threshold values B may be decided as desired.

In this example, the analyzing process S340 is performed for the data stored in the memory at the converted signal receiving process Step S310, but the data may be successively compared with the threshold values B, A, instead of being stored, to thereby detect the viable particle 35 or the non-viable particle 37, and detect the peak of the signal B in real time to find the particle size classification. Further, since the intensity of the signal A depending on the light amount of the autofluorescence light 35e also corresponds to the kind and an activation state of the viable particle, these pieces of information may be also found by detecting the peak of the signal A.

In the above-described manner, based on the signal A and the signal B, it is possible not only to detect whether or not the viable particle 35 exists in real time but also to measure the size of the viable particle 35. When the detection flag is set to ON as a result of the detection on the presence/absence of the viable particle 35, the counting process of the viable particles 35 is next performed by the analysis result outputting process Step S400.

[Result Outputting Device (Viable Particle Counting Apparatus)]

The result outputting device 330 is a device which counts the number of the viable particles 35 derived from the analysis by the data analyzing device 320 and transmits the count value to the notifying part 400.

[Analysis Result Outputting Process]

Figure 14:
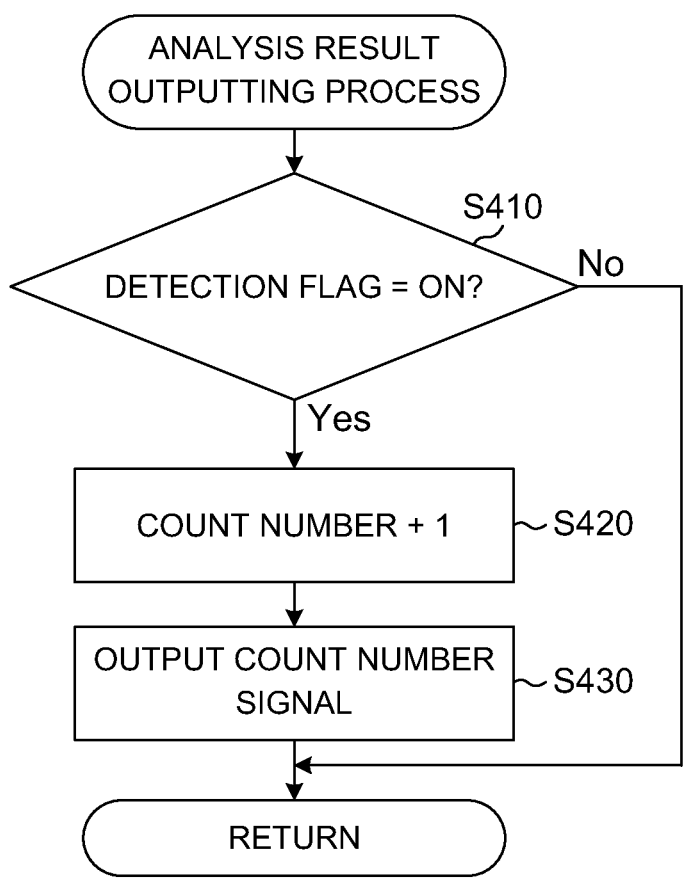
FIG. 14 is a flowchart illustrating a procedure example of an analysis result outputting process.

FIG. 14 is a flowchart illustrating a procedure example of the analysis result outputting process.

First, the result outputting device 330 receives the flag signal (detection flag) from the data analyzing device 320. Then, it determines whether or not the detection flag is set to ON (Step S410). When as a result the detection flag is ON (Step S410: Yes), it determines that the viable particle 35 is detected, and increments the count number by 1 to calculate the count value (Step S420). Then, the count value (count number) is transmitted to the notifying part 400 (Step S430). Here, when a reset button (not illustrated) is pressed or when a start button (not illustrated) is pressed, a process of resetting the count number, though not illustrated, may be executed before Step S410. Further, based on the received flag signal (size flag), the number of the viable particles 35 may be counted for each size of the viable particles 35.

[Notifying Part]

The notifying part 400 includes, for example, a display device 410 and a speaker 420.

[Notifying Process]

Figure 15:
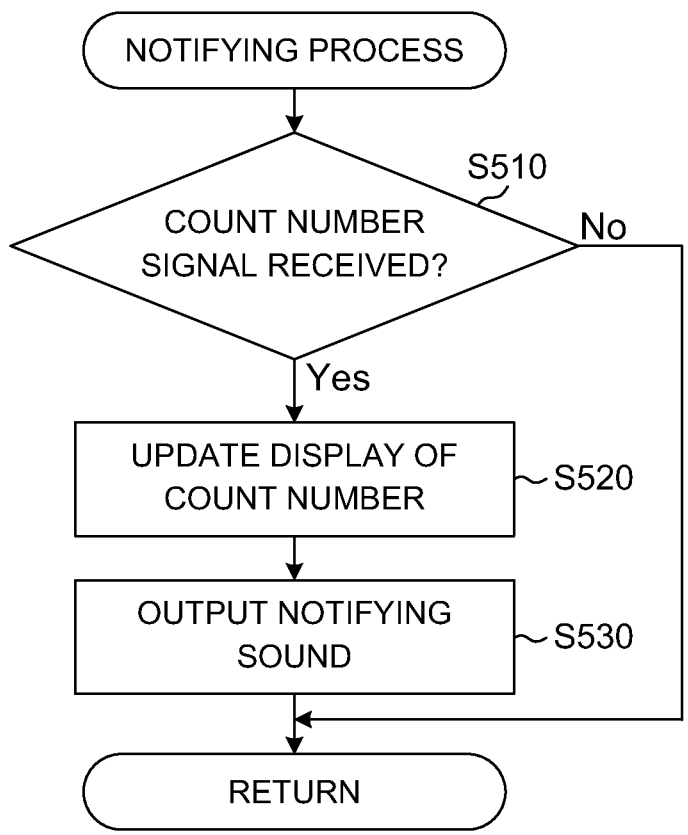
FIG. 15 is a flowchart illustrating a procedure example of a notifying process.

FIG. 15 is a flowchart illustrating a procedure example of the notifying process.

First, the notifying part 400 receives the count value transmitted by the result outputting device 330 of the data processing part 300 (Step S510). Next, the display on the display device 410 is updated to the received count value (Step S520).

Further, notifying sound is output from the speaker (Step S530). Here, the number of the detected viable particles 35 may be displayed on the display device 410 for each size of the viable particles 35. Another possible display form is to increment the count value by 1 in real time, or may be to display the updated count value a predetermined time later (for example, at five second interval).

An output manner of the notifying sound (the number of times the notifying sound is output, pitch of the notifying sound) may be changed according to a frequency with which the count value is incremented. Further, the output manner of the notifying sound may also be changed according to the size of the viable particle 35. For example, the output manner may be such that, when the count value of the viable particles 35 with 0.5 μm to 1.0 μm in unit time is 1 to 9, simple-interval sound is output once such as "Pi!", when this count value is 10 to 99, simple-interval sound is output twice such as "Pi! Pi!", and when this count value is 100 or more, simple-interval sound is output three times such as "Pi! Pi! Pi!".

Figure 16:
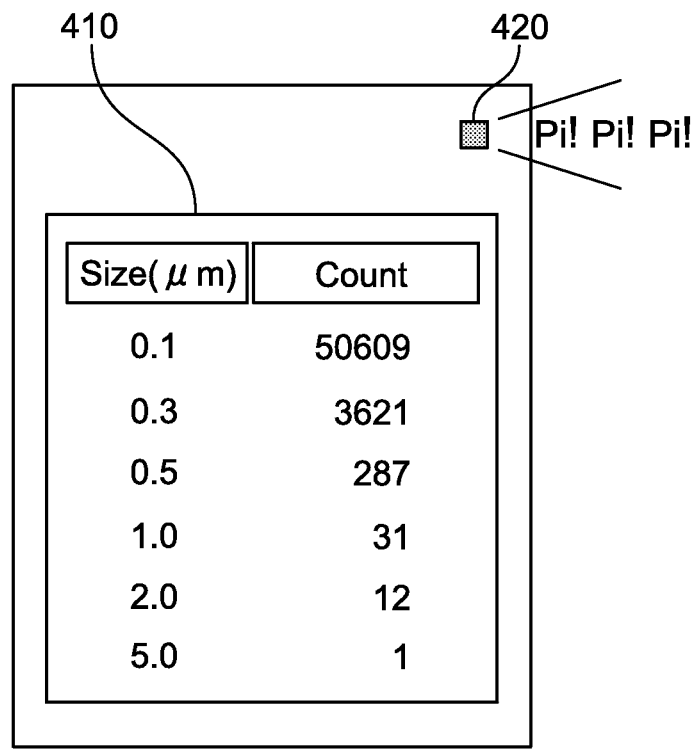
FIG. 16 is a view illustrating an example of the notification of a counting result of viable particles.

FIG. 16 is a view illustrating an example of the display device 410 and the speaker 420 which notify the counting result of the viable particles 35. As the display device, there are provided a display panel 410 which notifies the counting result for each size of the viable particles 35 and the speaker 420 which notifies that the viable particle 35 is detected by means of sound. For example, the display panel 410 includes a display part for "Size (m)" representing a reference of the size of the viable particles 35 and a display part for "Count" representing the number of the detected viable particles 35 corresponding to each size (count value). On the display part for "Size (μm)" representing the reference of the size of the viable particles 35, for example, six values "0.1", "0.3", "0.5", "1.0", "2.0", and "5.0" are displayed in advance. Regarding these values, "0.1" corresponds to a 0.1 μm to 0.3 μm size of the viable particles 35, "0.3" corresponds to a 0.3 μm to 0.5 μm size of the viable particles 35, "0.5" corresponds to a 0.5 μm to 1.0 μm size of the viable particles 35, "1.0" corresponds to a 1.0 μm to 2.0 μm size of the viable particles 35, "2.0" corresponds to a 2.0 μm to 5.0 μm size of the viable particles 35, and "5.0" corresponds to a 5.0 μm size of the viable particles 35 or more.

Therefore, it is shown that 50,609 pieces of the viable particles 35 whose size is 0.1 μm to 0.3 μm are counted, 3,621 pieces of the viable particles 35 whose size is 0.3 μm to 0.5 μm are counted, 287 pieces of the viable particles 35 whose size is 0.5 μm to 1.0 μm are counted, 31 pieces of the viable particles 35 whose size is 1.0 μm to 2.0 μm are counted, 12 pieces of the viable particles 35 whose size is 2.0 μm to 5.0 μm are counted, and 1 piece of the viable particle 35 whose size is 5.0 μm or larger is counted.

As described above, the notifying part 400 is capable of notifying the count value of the viable particles 35 in real time by the display device 410 and outputting the notifying sound from the speaker 420 when the viable particles 35 are detected. Incidentally, the notifying part 400 may be additionally provided with an external output terminal and may output the data to another apparatus through the terminal.

Note that the device 70 which selects the autofluorescence light of the viable particle, included in the light detecting system 1, is not limited to the long-pass filter 70 but may be formed by a dichroic mirror. For example, a dichroic mirror which transmits a light having a wavelength longer than the 490 nm cutoff wavelength and reflects a light with a wavelength shorter than the 490 nm cutoff wavelength may be provided. As a result, a light having a wavelength shorter than 490 nm (mainly the scattered light from the viable particle 35 or the non-viable particle 37) is received by the second light receiving device (photodiode) 110. On the other hand, a light having a wavelength longer than 490 nm (mainly the autofluorescence light 35e from the viable particle 35e) is received by the first light receiving device (photo multiplier tube) 90.

Besides, regarding the device 60 which reflects the scattered light and the device 70 which selects the autofluorescence light, of the light detecting system 1, instead of installing the device 70 on a subsequent stage of the device 60, the device 60 and the device 70 may be installed in parallel so that light paths of the scattered light and the autofluorescence light become separate systems. In this case, a short-pass filter which transmits only a light whose wavelength is shorter than the 410 nm cutoff wavelength is used as the device 60. Then, the condensing lens optical systems which gather the scattered light and the autofluorescence light 35e from the flow cell, and the second light receiving device (photodiode) 110 and the first light receiving device (photomultiplier tube) 90 are installed in front of and at the back of the respective optical devices. Consequently, for example, owing to the short-pass filter 60 installed at a 90 degree position (horizontal plane) from the optical axis of the laser light 31 and using 410 nm as a reference, the photodiode 110 can detect mainly the scattered light from the viable particle 35 or the non-viable particle 37, and owing to the long-pass filter 70 installed at a 90 degree position (vertical plane) from the optical axis of the laser light 31 and using 490 nm as the cutoff wavelength, the photo multiplier 90 can detect mainly the autofluorescence light 35e from the viable particle 35.

As described above, according to this embodiment, it is possible to improve counting accuracy of the viable particles 35. For this purpose, the detection of the autofluorescence light 35e emitted from the viable particle 35 being a detection (measurement) target is used as an index. The emission of the autofluorescence light 35e is caused by radiating the laser light 31 to a substance necessary for metabolism of life activity occurring in a living organism, such as riboflavin and NAD(P)H in the cell of the viable particle 35. Incidentally, the wavelength of the laser light 31 differs depending on the substance emitting the autofluorescence light, and the optimum wavelength is used. Further, when the laser light 31 is radiated, the Raman-scattered light 33s from water and the scattered light from the viable particle 35 are emitted, besides the autofluorescence light from the viable particle. Therefore, in this embodiment, the dichroic mirror and the long-pass filter are provided. Consequently, the scattered light from the viable particle 35 can be reflected by the dichroic mirror, and by the long-pass filter, the Raman-scattered light 33s by water can be reduced and the autofluorescence light 35e from the viable particle 35 can be transmitted.

Therefore, according to the counting apparatus 77 and the counting method of this embodiment, it is possible to count the viable particles existing in the flowing liquid with high accuracy. Further, the autofluorescence light emitted from the viable particle can be efficiently detected even in a state where the Raman-scattered light by the water is generated.

[Case where Dialysis Fluid is Detection Target Liquid]

Next, an embodiment of a case where a counting apparatus 77 handles a dialysis fluid as a liquid whose viable particles are detection targets will be concretely described. That is, a case where a dialysis fluid administered to a human body is used as a liquid made to flow in a device 30 which makes a target flow therein, of the counting apparatus 77 will be concretely described.

Figure 17:
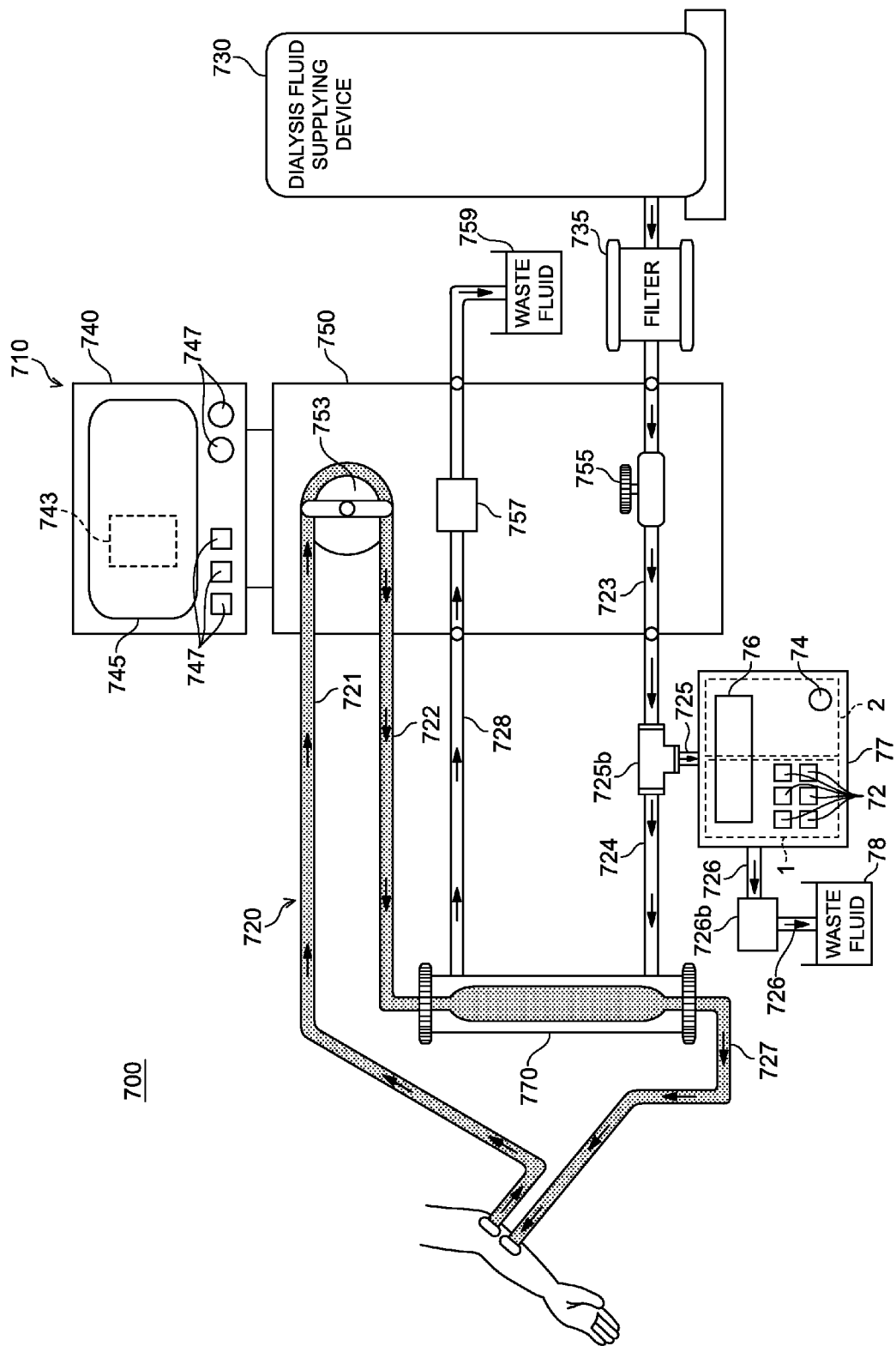
FIG. 17 is an explanatory diagram of a system relating to dialysis fluid inspection in blood dialysis.

FIG. 17 is an explanatory diagram of a system relating to dialysis fluid inspection in blood dialysis.

As illustrated in FIG. 17, the blood dialysis of a patient is executed by a blood dialyzing apparatus 700, and the counting apparatus 77 executes the determination on whether or not viable particles exist in the dialysis fluid used in the blood dialysis and the counting of the number of the viable particles. Therefore, the blood dialyzing apparatus 700 will be concretely described. Note that the counting apparatus 77 of this embodiment is usable not only for the dialysis fluid in the blood dialyzing apparatus 700 but also for a dialysis fluid in a blood filtering apparatus.

[Blood Dialyzing Apparatus]

The blood dialyzing apparatus 700 includes: a dialysis monitoring apparatus 710 which monitors and adjusts patient information, the flows of the blood and the dialysis fluid, and so on; a distributing circuit 720 in which the blood and the dialysis fluid flow; a blood purifier 770 which diffuses deficient matter from the dialysis fluid to the blood while expelling waste products in the blood; and a dialysis fluid supplying device 730 which supplies the dialysis fluid.

[Dialysis Monitoring Apparatus]

The dialysis monitoring apparatus 710 includes a controlling and monitoring part 740 and a distribution adjusting part 750. The controlling and monitoring part 740 is an apparatus which controls and monitors the blood dialysis in general, and includes a controlling and monitoring device 743, a display part 745 (notifying device), and an operation part 747. The controlling and monitoring device 743 performs the distribution adjustment of the blood collected from the patient and the blood administered after the blood dialysis, the adjustment of temperature and distribution of the dialysis fluid sent out from the dialysis fluid supplying device 730 to the blood purifier 770, the monitoring of a body condition (for example, blood pressure, electrocardiogram information, and so on) of the patient, the distribution and monitoring of the dialysis fluid before and after the blood dialysis, and so on. The display part 745 (notifying device) displays various kinds of information, a progress status, input data, and so on. The operation part 747 accepts an operation from the outside of the apparatus (for example, a medical worker).

Concretely, the controlling and monitoring device 743 includes a CPU which executes various kinds of processing, a ROM storing the processing contents (program and data), a RAM storing various kinds of information, and so on. Further, the display part 745 is a display and displays information output from the controlling and monitoring device 743. Further, the operation part 747 is composed of, for example, a plurality of input buttons, and is capable of accepting instructions of the processing and accepting input and output of information when a predetermined operation button is pressed by a medical worker. Further, an external connection terminal, though not illustrated, which accepts a control signal from the outside of the apparatus and outputs various kinds of information may be provided.

[Distribution Adjusting Part]

The distribution adjusting part 750 includes a blood pump 753, a dialysis fluid regulating valve 755, and a discharging device 757. The blood pump 753 adjusts a flow rate of the blood collected from the patient and circulates the blood. The dialysis fluid regulating valve 755 adjusts a flow rate of the dialysis fluid supplied from the dialysis fluid supplying device 730. The discharging device 757 discharges the dialysis fluid discharged from the blood purifier 770. These blood pump 753, dialysis fluid regulating valve 755, and discharging device 757 are controlled by the aforesaid controlling and monitoring device 743. Incidentally, the dialysis fluid discharged to the outside of the dialysis monitoring apparatus 710 from the discharging device 757 is made to flow to a waste fluid disposal part 759 and thereafter undergoes waste fluid disposal.

[Distributing Circuit]

The distributing circuit 720 includes blood circuits 721, 722, 727 and dialysis fluid circuits 723, 724, 725, 726, 728.

[Blood Circuits]

The blood circuit 721 connects an artery of the patient and a blood inlet port of the blood pump 753 and makes the blood collected from the patient flow to the blood pump 753. The blood circuit 722 connects a blood outlet port and a blood inlet port of the blood purifier 770 and makes the blood sent out from the blood pump 753 flow to the blood purifier 770. The blood circuit 727 connects a blood outlet port of the blood purifier 770 and a vein of the patient and administers the blood having undergone the blood dialysis by the blood purifier 770 to the vein of the patient. A flow rate of the blood flowing in the blood circuits 721, 722, 727 is adjusted by the blood pump 753, and for example, the blood at a flow rate of about 200 ml/min circulates.

[Dialysis Fluid Circuits]

The dialysis fluid circuit 723 makes the dialysis fluid supplied from the dialysis fluid supplying device 730 flow therein. Incidentally, in the middle of the dialysis fluid circuit 723, the dialysis fluid regulating valve 755 which adjusts a flow rate of the dialysis fluid is provided. Before being made to flow into a dialysis fluid inlet port of the blood purifier 770, the dialysis fluid flowing in the dialysis fluid circuit 723 is made to branch off by a dialysis fluid divider 725b (dividing device) in order for the viable particles in the dialysis fluid to be counted. Concretely, after branching off, part of the dialysis fluid flowing in the dialysis fluid circuit 723 is made to flow to the dialysis fluid circuit 725 to be thereafter sent to the counting apparatus 77. On the other hand, most of the dialysis fluid flowing in the dialysis fluid circuit 723 is made to flow to the dialysis fluid circuit 724 to be made to flow into the dialysis fluid inlet port of the blood purifier 770. The dialysis fluid circuit 726 makes the dialysis fluid having undergone the detecting and counting processes of the viable particles in the counting apparatus 77 flow to a waste fluid disposal device 78, and the dialysis fluid is disposed of as a waste fluid in the waste fluid disposal device 78. The dialysis fluid circuit 728 makes the dialysis fluid sent out from a dialysis fluid outlet port of the blood purifier 770 flow therein. Incidentally, in the middle of the dialysis fluid circuit 728, the discharging device 757 which sends the dialysis fluid to the waste fluid disposal device 759 is provided. After the flow rate of the dialysis fluid made to flow in these dialysis fluid circuits 723, 724, 725, 726, 728 is adjusted by the regulating valve 755 and the counting apparatus 77, the dialysis fluid is made to flow to the blood purifier 770. For example, the dialysis fluid at a flow rate of about 500 ml/min is made to flow into the blood purifier 770, and the dialysis fluid at a flow rate of about 10 ml/min is made to flow into the counting apparatus 77.

[Dialysis Fluid Supplying Device]

The dialysis fluid supplying device 730 is a device which supplies the dialysis fluid, and concretely is a storage tank. For example, the dialysis fluid is stored in the tank, and the dialysis fluid can be supplied to the blood purifier 770 and the counting apparatus 77 by the regulating valve 755 in the dialysis monitoring apparatus 710 being operated. Further, a filter 735 is installed between the dialysis fluid supplying device 730 and the blood purifier 770, and there, the dialysis fluid before it flows into the blood purifier 770 is finally purified.

[Blood Purifier]

The blood purifier 770 is, for example, a device which purifies the blood collected from the patient and concretely is a blood dialyzer. Incidentally, when it is a blood filtering apparatus, a blood filter (hemofilter) is used instead. In this embodiment, a description will be given assuming that the blood dialyzer 770 is used as the blood purifier.

The dialyzer 770 includes the outlet and inlet ports of the blood and the outlet and inlet ports of the dialysis fluid. Connection destinations of the inlet ports and the outlet ports of the dialyzer 770 are as follows. The blood inlet port is connected to the blood circuit 722, the blood outlet port is connected to the blood circuit 727, the dialysis fluid inlet port is connected to the dialysis fluid circuit 724, and the dialysis fluid outlet port is connected to the dialysis fluid circuit 728. Further, the dialyzer 770 includes a plurality of (for example, several thousand) hollow fiber membranes allowing the blood to flow therein. Therefore, the blood flowing into the dialyzer 770 from the blood inlet port connected to the blood circuit 722 branches off into the several thousand hollow fiber membranes. Thereafter, the blood having undergone the blood dialysis via the hollow fiber membranes is sent out to the blood circuit 727 from the blood outlet port. Then, the dialysis fluid flowing into the dialyzer 770 from the dialysis fluid inlet port connected to the dialysis fluid circuit 724 is made to flow in a direction opposite that of the blood to the outer sides of the plural hollow fiber membranes. Thereafter, the dialysis fluid having undergone the blood dialysis via the hollow fiber membranes is made to flow out to the dialysis fluid circuit 728 from the dialysis fluid outlet port. Inside the dialyzer 770, the waste products in the blood move into the dialysis fluid flowing outside the hollow fiber membranes and the deficient components in the blood move into the blood through the hollow fiber membranes from the dialysis fluid.

[Viable Particle Counting Apparatus for Dialysis]

The counting apparatus 77 supplied with the dialysis fluid from the dialysis fluid supplying device 730 may further include operation parts 72, 74 and a notification display 76 (notifying device) in addition to a light detecting system 1 and an autofluorescence light counting system 2 as described above. The light detecting system 1 is an apparatus which radiates a light to a target (dialysis fluid) to detect a scattered light and an autofluorescence light from the target. The autofluorescence light counting system 2 is an apparatus which counts the number of the autofluorescence lights based on signals output from the light detecting system 1. The operation parts 72, 74 are composed of, for example, a plurality of kinds of buttons 72 and a controller 74 respectively, and are capable of accepting an operation of the counting apparatus 77 by a medical worker. Further, the notification display 76 is capable of displaying, for example, input information, operation information, and so on besides the counting result notified by a notifying part 400.

Concretely, in the counting apparatus 77, the dialysis fluid supplied from the dialysis fluid supplying device 730 first flows in the device 30 which makes the target flow therein, and a laser light having a 375 nm to 420 nm wavelength easily exciting riboflavin is radiated to the flowing dialysis fluid from a light emitting device 10. Thereafter, as described above (refer to FIG. 1), due to an interaction of the radiated laser light with water (water molecules) of the dialysis fluid flowing in the device 30 which makes the target flow therein and with the target (a viable particle 35 or a non-viable particle 37), the scattered light, the Raman-scattered light, and the autofluorescence light are emitted to the surroundings. Then, these lights pass through a plurality of condensing lens systems 40, 80, 100 and devices which select lights based on wavelength (device 60, device 70) to be detected by light receiving devices (device 90, device 110). Further, as described above (refer to FIG. 8 and FIG. 9), as for the Raman-scattered light emitted from the water of the dialysis fluid and the autofluorescence light, most of the Raman-scattered light by the water is cut off by, for example, the long-pass filter 70 using a cutoff wavelength (for example, 490 nm) as a reference, while the autofluorescence light is transmitted. Thereafter, detection signals of the device 110 and the device 90 are transmitted to the autofluorescence light counting system 2, and based on the transmitted data, the presence/absence of the viable particle 35 is confirmed in real time, and the viable particles 35 are counted for each particle size. Then, finally, the counting result is displayed on the notification display 76 or output to the outside.

Incidentally, it is preferable to provide, for example, a suction pump or a flow rate regulating valve 726b inside the counting apparatus 77 or on the dialysis fluid circuit 726. When the adjustment of a supply amount of the dialysis fluid by the dialysis fluid supplying device 730 is not sufficient, providing these makes it possible to facilitate the adjustment.

Note that the liquid as the detection target is not limited to the dialysis fluid for the blood dialysis and the blood filtration. For example, the liquid may be an intravenous drip administered to a human body. Note that if the liquid is a transparent liquid mostly made of water, it is possible to similarly perform the detection of the presence/absence of the viable particles and the counting of the viable particles in real time.

As described above, according to this embodiment, by using the counting apparatus 77, it is possible to determine in real time whether or not the viable particle 35 exists regarding the dialysis fluid. Note that in the determination on the presence/absence of the viable particles regarding the dialysis fluid as well, the detection of the autofluorescence light 35e is used as an index. The autofluorescence light 35e is emitted from an autofluorescent substance required for metabolism of life activity occurring in a living organism, such as riboflavin and NAD(P)H in a cell of the viable particle 35 being the detection (measurement) target. When as a result of the counting by the counting apparatus 77, it is confirmed that a prescribed number of the viable particles 35 or more exist in the dialysis fluid for which the counting is performed, the result is notified to the outside from a notifier provided in the counting apparatus 77. For example, it is possible to output notifying sound from a speaker and perform the display on the display 745 of the dialysis monitoring apparatus 710 or a later-described central monitoring and control apparatus 640. This makes it possible to take a quick measure to the dialysis fluid before the contamination by the viable particles progresses (before a count value of the viable particles becomes abnormal) and to reduce an influence on the patient to the minimum.

Next, a dialysis fluid monitoring system including this counting apparatus 77 will be described.

[Dialysis Fluid Monitoring System Including Viable Particle Counting Apparatus]

Figure 18:
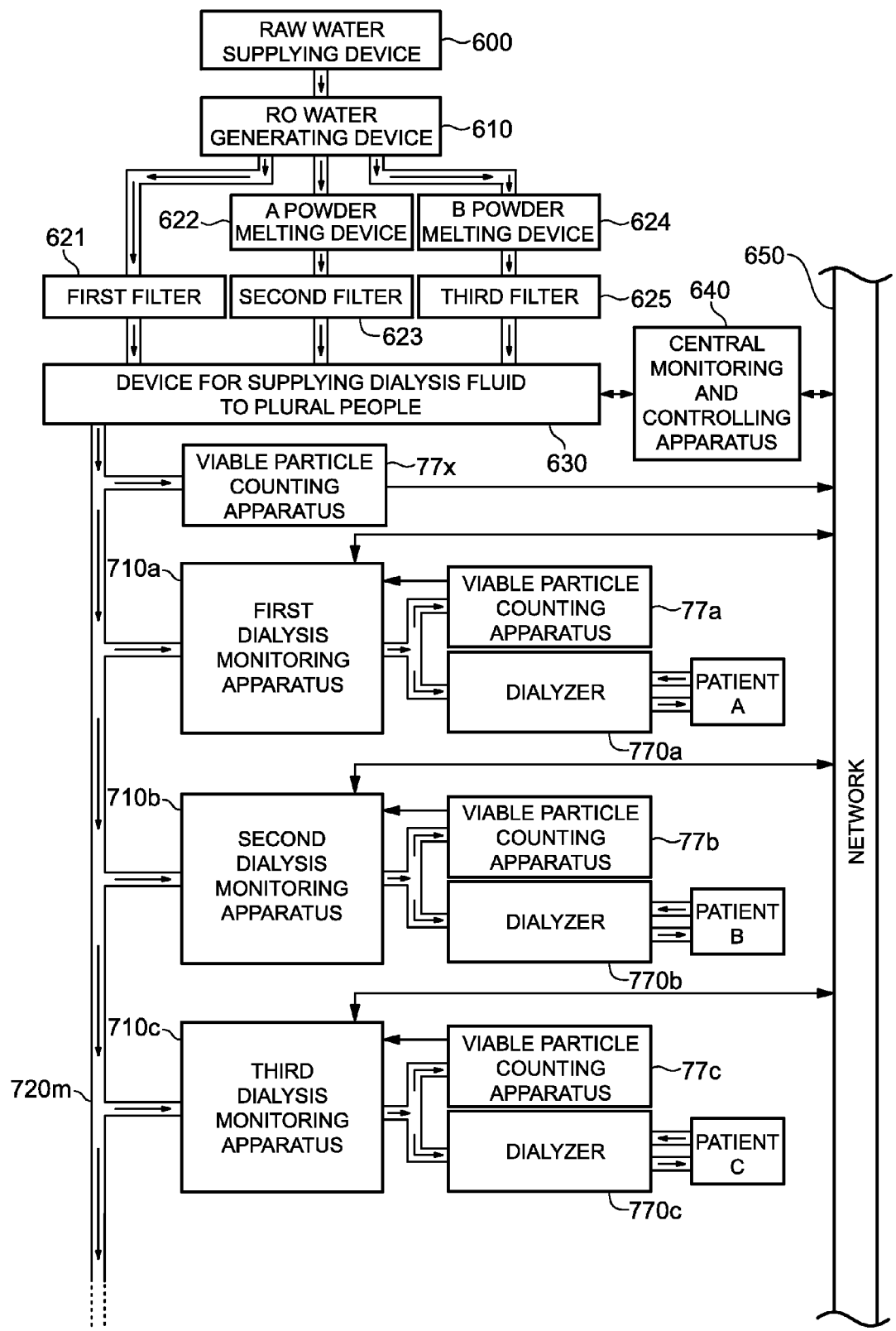
FIG. 18 is an explanatory diagram of a system of an artificial dialysis apparatus for many people.

FIG. 18 is an explanatory diagram of an artificial dialysis apparatus system for many people.

As illustrated in FIG. 18, the artificial dialysis apparatus system for many people includes a system which performs blood dialysis and a dialysis fluid monitoring system. The system which performs blood dialysis performs blood dialyses of a plurality of patients at the same time by using one device 630 which supplies the dialysis fluid to a plurality of people. The dialysis fluid monitoring system determines whether or not viable particles exist in the dialysis fluid by counting apparatuses 77 installed at various places.

The dialysis fluid used by the artificial dialysis apparatus system for many people is manufactured through a plurality of steps. First, a RO water generating device 610 removes ions and other organic matter from water of a raw water supplying device 600 (for example, a tap water), so that purified RO water (water purified by a reverse osmosis membrane (RO membrane), what is called pure water)) is manufactured. Then, by using the RO water, an A diluting solution for dialysis is manufactured by an A powder melting device 622 and a B diluting solution for dialysis is manufactured by a B powder melting device 624. Finally, the RO water purified by a first filter 621, the A diluting solution for dialysis purified by a second filter 623, and the B diluting solution for dialysis purified by a third filter 625 are mixed, whereby the dialysis fluid is manufactured. The dialysis fluid thus manufactured is stored in the device 630 which supplies the dialysis fluid to a plurality of people (step of supplying the dialysis fluid to a plurality of people).

The dialysis fluid stored in the device 630, for example, flows in a fluid distribution pipe 720*m* for dialysis (a liquid distributer for many people) to branch off to a first dialysis monitoring apparatus 710*a*, a second dialysis monitoring apparatus 710*b*, a third dialysis monitoring apparatus 710*c*, . . . (step of distributing the liquid to a plurality of people). Then, the dialysis fluid flows into dialyzers 770*a*, 770*b*, 770*c* connected to the respective dialysis monitoring apparatuses 710*a*, 710*b*, 710*c*. Further, bloods collected from patients A, B, C undergo blood dialysis in the dialyzers 770*a*, 770*b*, 770*c*, and thereafter the purified bloods are administered to the patients.

Incidentally, it is assumed here that the blood dialyses for the plural patients are monitored by the central monitoring and controlling apparatus 640 (device which collects the determination results on the presence/absence of the viable particles for many people). Concretely, pieces of information transmitted from the respective dialysis monitoring apparatuses 710*a*, 710*b*, 710*c* are received by the central monitoring and controlling apparatus 640 via a network 650 in real time and the monitoring is performed based on these pieces of information (step of collecting the determination results on the presence/absence of the viable particles for many people).

Further, in this example, the counting apparatuses 77 installed at various places determine whether or not the viable particles exist in the dialysis fluid. For example, it is determined whether or not the viable particles exist in the dialysis fluid before the bloods having undergone the blood dialysis using the dialysis fluid are administered to the patients A, B, C, that is, before the dialysis fluid is made to flow into the dialyzers 770*a*, 770*b*, 770*c*. This determination is made possible by providing viable particle counting apparatuses 77*a*, 77*b*, 77*c* between the dialysis monitoring apparatuses 710*a*, 710*b*, 710*c* and the dialyzers 770*a*, 770*b*, 770*c*. Further, the counting results of the counting apparatuses 77*a*, 77*b*, 77*c* are transmitted to the respective dialysis monitoring apparatuses 710*a*, 710*b*, 710*c* and then transmitted from the dialysis monitoring apparatuses 710*a*, 710*b*, 710*c* to the central monitoring and controlling apparatus 640 via the network 650.

For example, when, as a result of the counting by any of the counting apparatuses 77, it is confirmed that a prescribed number of the viable particles or more exist in the dialysis fluid for which the counting is performed, a notifying device provided in the counting apparatus 77 notifies the confirmation result to the outside. For example, notifying sound is output from a speaker, or the display indicating a state of the dialysis fluid is made on the display 745 (notifying device) of the dialysis monitoring apparatus 710 or the central monitoring and controlling apparatus 640. Consequently, it is possible to confirm that the viable particles exist in the dialysis fluid in real time at a site where the blood dialysis is executed. As a result, it is possible to take a quick measure to the dialysis fluid before the contamination by the viable particles progresses, which can reduce an influence on the patient to the minimum.

Besides, the counting apparatuses 77 may be installed in the supplying device 630 and the fluid distribution pipe 720*m* for dialysis (device which distributes the liquid to a plurality of people). Consequently, it is possible to directly inspect the dialysis fluid distributed from the supplying device 630. Further, the counting apparatuses 77, not illustrated, may be provided in front of and at the back of the RO water generating device 610, the A powder melting device 622, the B powder melting device 624, the first filter 621, the second filter 623, and the third filter 625. Consequently, it is possible to confirm which of the devices or which of the pipes between the device and the device is contaminated by the viable particles.

According to the above-described embodiment of the system, the counting apparatuses 77 are provided at various places in the artificial dialysis apparatus system for many people, such as the dialysis monitoring apparatuses 710, and the counting results by these are transmitted to the central monitoring and controlling apparatus 640 via the network 650. Since it is possible to confirm that the viable particles exist in the dialysis fluid in real time regarding the blood dialyses performed at a plurality of places, it is possible to take a quick measure to the dialysis fluid when a trouble occurs, which can reduce the influence to the patient to the minimum.

[Case where Purified Water is Detection Target Liquid]

Next, an embodiment in a case where water having undergone purification treatment is handled as a liquid in which viable particles are to be detected by a viable particle counting apparatus 77 will be described. That is, water having undergone purification treatment is made to flow in an device 30 which makes a target flow therein. Besides, by additionally providing a counting apparatus 77, water under the purification treatment may be made to flow in its device 30 which makes a target flow therein.

Figure 19:
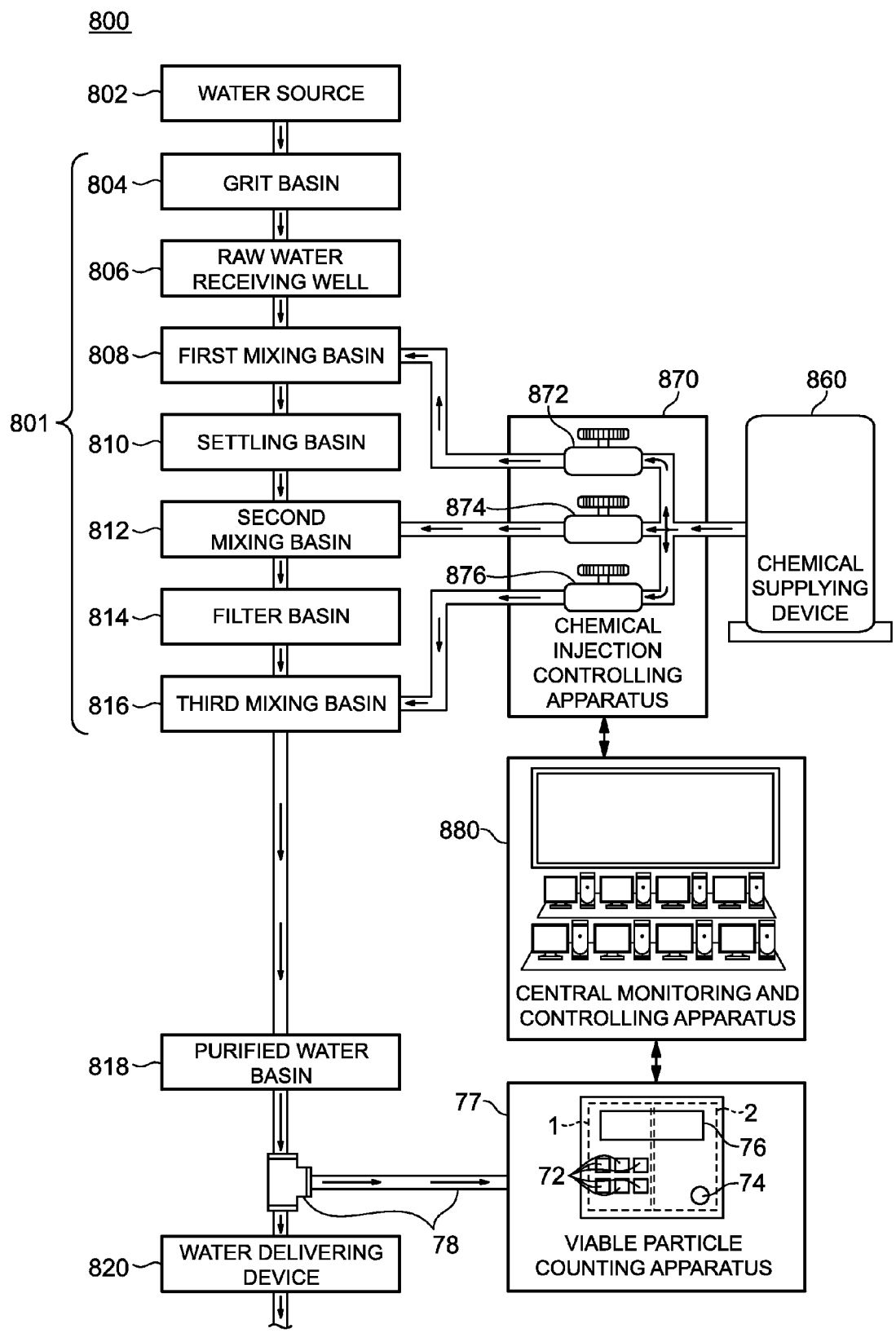
FIG. 19 is an explanatory diagram of a system relating to viable particle inspection of purified water in a water purification plant.

FIG. 19 is an explanatory diagram of a system relating to the inspection of viable particles in purified water in a water purification plant.

As illustrated in FIG. 19, regarding the purified water having undergone the purification treatment by a water purifying system 800 in the water purification plant, the counting apparatus 77 inspects and determines whether or not the viable particles exist. Further, the number of the viable particles is counted. The water purifying system 800 will be concretely described.

[Water Purifying System]

The water purifying system 800 is composed of a plurality of purifying basins 801 (various kinds of basins being targets of the purification treatment) where the purification treatment is performed, a purified water basin 818 storing the manufactured purified water in the water purification plant, a water delivering device 820 which delivers the manufactured purified water, a chemical supplying device 860, a chemical injection controlling apparatus 870, a central monitoring and controlling apparatus (system controlling apparatus) 880, and so on. Further, the plural purifying basins 801 (various kinds of basins being targets of the purification treatment) include, for example, a grit basin 804, a raw water receiving well 806, a first mixing basin 808, a settling basin 810, a second mixing basin 812, a filter basin 814, a third mixing basin 816, and so on. The water purifying system 800 purifies raw water taken from a water source 802 by these constituent elements to manufacture the purified water. Hereinafter, the constituent elements will be concretely described.

[Central Monitoring and Controlling Apparatus (System Controlling Apparatus)]

The central monitoring and controlling apparatus 880 is composed of a plurality of computers and is an apparatus which monitors and controls the whole purification treatment performed in the water purifying system 800. Concretely, the central monitoring and controlling apparatus 880 performs the control for purifying the raw water to manufacture clean purified water, such as controlling the purification treatment, the adjustment of a water amount, the monitoring of water quality, water delivery, and so on. Here, the purification treatment means to purify the water in purifying basins 804 to 816 and so on. Further, the adjustment of a water amount and the monitoring of water quality mean the adjustment of a water amount and the monitoring of a purification state and so on at the time of the water purification performed in the purifying basins 804 to 816 and so on. Further, the water delivery means to deliver the water having undergone the purification treatment to the next purifying basin. Incidentally, the manufactured purified water is once stored in the purified water basin 818 and is thereafter delivered to distribution reservoirs of respective areas by the water delivering device 820. Further, the central monitoring and controlling apparatus 880 also controls the chemical injection controlling apparatus 870. The chemical injection controlling apparatus 870 adjusts an injection amount of chemicals used when the water is disinfected in the first mixing basin 808, the second mixing basin 812, and the third mixing basin 816. In these first mixing basin 808, second mixing basin 812, and third mixing basin 816, the raw water taken from the water source 802 is purified step by step, and through these mixing basins, the purified water is finally manufactured. Hereinafter, concrete purification treatments in the constituent elements will be described.

[Grit Basin]

In the grit basin 804, the raw water taken from the water source 802 is pooled. For example, when the water source 802 is a river, the taken raw water contains large dusts, sands, soil, and so on. Therefore, while the raw water is pooled in the grit basin 804, the large dusts are removed, and the sands and soil are settled in a bottom of the grit basin 804, resulting in a certain degree of purification. The water from which the large dusts, sands, and soil are eliminated is next sent to the raw water receiving well 806 by an intake pump or the like.

[Raw Water Receiving Well]

In the raw water receiving well 806, the water sent from the grit basin 804 is pooled. Here, when raw waters are taken from a plurality of water sources 802, the waters pooled in a plurality of grit basins 804 corresponding to the respective water sources are combined in this raw water receiving well 806. Then, this raw water receiving well 806 adjusts a flow rate of the water that is to be sent to the first mixing basin 808 based on a level and an amount of the pumped-up water.

[First Mixing Basin]

In the first mixing basin 808, mainly, the water sent from the raw water receiving well 806 and a flocculant are mixed. Incidentally, sodium hypochlorite (hereinafter referred to as chlorine) used for sterilization or the like is sometimes injected. The flocculant is, for example, poly aluminum chloride or the like. Using a stirring apparatus for the mixture with the flocculant facilitates mixing fine sands, soil, and so on with the flocculant. Further, by adjusting a stirring speed, they are flocculated separately for each kind such as small contaminants, turbidity components, and so on. The water mixed with the flocculant is next sent to the settling basin 810.

[Settling Basin]

In the settling basin 810, the small contaminants and the turbidity components contained in the water are flocculated by the flocculant mixed in the first mixing basin 808, to settle. The small contaminants include dusts, mud, organic matter, plankton, and so on. The water from which the lumped deposits are removed or a supernatant of the water pooled in the settling basin 810 is next sent to the second mixing basin 812.

[Second Mixing Basin]

In the second mixing basin 812, the water sent from the settling basin 810 is supplied with, for example, chlorine. The chlorine is supplied from the chemical supplying device 860 via the chemical injection controlling apparatus 870. Consequently, the viable particles contained in the water pooled in the second mixing basin 812 reduce. The chlorinated water is next sent to the filter basin 814.

[Filter Basin]

In the filter basin 814, the water sent from the second mixing basin 812 passes through sands and gravels, and further fine dusts, turbidity components, and so on are filtered out. The filtered water is next sent to the third mixing basin 816.

[Third Mixing Basin]

In the third mixing basin 816, the water sent from the filter basin 814 is chlorinated by the chlorine being injected again to this water. This chlorine is also supplied from the chemical supplying device 860 via the chemical injection controlling apparatus 870. Therefore, the viable particles contained in the water pooled in the third mixing basin 816 further reduce. Incidentally, in order to keep safety of the purified water until it is sent to an end (for example, a water tap of a house), this chlorination is important purification treatment. Therefore, the chlorine with an amount large enough to eliminate the viable particles (for example, cryptosporidium or the like) liable to affect a human body is injected. Finally, the chlorinated purified water is next sent to the purified water basin 818.

[Purified Water Basin]

In the purified water basin 818, the purified water sent from the third mixing basin 816 is pooled. Here, the quality of the purified water manufactured by the purification treatments so far is examined. In this embodiment, regarding the purified water pooled in the purified water basin 818, the counting apparatus 77 determines whether or not the viable particles exist in the purified water, and at the same time counts the number of the viable particles.

[Water Delivering Device]

The water delivering device 820 is, for example, a pressurizing-type water pump 820 and is a device which delivers the purified water pooled in the purified water basin to distribution reservoirs in various areas through water distribution pipes.

As described above, the water purifying system 800 purifies the raw water taken from the water source 802 by the plural purification treatments in the plural purifying basins 804 to 816. The purified water manufactured through the purification is delivered to various areas from the purified water basin 818 by the water delivering device 820. Here, the chlorination in the purification treatment by the water purifying system 800 will be concretely described.

[Chemical Supplying Device]

The chemical supplying device 860 is, for example, a storage tank and stores the sodium hypochlorite (chlorine) or the like used at the time of the chlorination. In the illustrated example, it branches off from the single storage tank 860 into the first mixing basin 808, the second mixing basin 812, and the third mixing basin 816, where the sterilization and so on are performed. The device 860 may be a device capable of further supplying the flocculant or the like, and the storage tank 860 may be provided per each of the mixing basins 808, 812, 816. The chlorine or the like supplied from the storage tank 860 is supplied to the mixing basins 808, 812, 816 via water distribution pipes, and the chemical injection controlling apparatus 870 provided in the middle of the water distribution pipes adjusts a flow rate of the injected chlorine.

[Apparatus which Controls Injection of Chemicals]

The apparatus 870 which controls the injection of the chemicals is provided with regulating valves which adjust flow rates of the chlorine or the like supplied from the storage tank 860 via the water distribution pipes.

For example, a regulating valve 872 is connected to the water distribution pipe between the storage tank 860 and the first mixing basin 808, a regulating valve 874 is connected to the water distribution pipe between the storage tank 860 and the second mixing basin 812, and a regulating valve 876 is connected to the water distribution pipe between the storage tank 860 and the third mixing basin 816. The regulating valves 872, 874, 876 adjust the flow rates of the chlorine or the like flowing in the water distribution pipes. Incidentally, the adjustment of the flow rate by each of the regulating valves 872, 874, 876 is performed based on an instruction from the central monitoring and controlling apparatus 880.

In the above-described manner, the chlorine is injected to the mixing basins 808, 812, 816, so that the chlorination is performed. Further, the chlorinated water is sent to the purified water basin 818. The purified water sent to the purified water basin 818 is sent by a dividing device 78 to the counting apparatus 77, where it is determined whether or not the viable particles exist in the purified water.

[Dividing Device]

The dividing device 78 includes, for example, a water distribution pipe which makes the purified water from the purified water basin 818 branch off to lead the branching purified water to the counting apparatus 77, and when necessary, includes a suction pipe (not illustrated), a flow rate regulating valve (not illustrated) adjusting a flow rate in the water distribution pipe, and so on. Then, the purified water inspected by the counting apparatus 77 is discharged from a water distribution pipe on a discharge side. Incidentally, when the suction pump and the flow rate regulating valve are necessary, they are preferably provided in the discharge-side water distribution pipe of the counting apparatus 77. For example, when the purified water cannot be stably led to the counting apparatus 77, the flow rate of the purified water can be easily adjusted by providing these.

[Viable Particle Counting Apparatus for Purified Water]

The counting apparatus 77 supplied with the purified water from the dividing device 78 may further include operation parts 72, 74 and a notification display 76 (notifying device) besides a light detecting system 1 and an autofluorescence light counting system 2 as described above. As described above, the light detecting system 1 is an apparatus which radiates a light to the purified water to detect a scattered light and an autofluorescence light from the target. The autofluorescence light counting system 2 is an apparatus which counts the number of the autofluorescence lights based on signals output from the light detecting system 1. The operation parts 72, 74 are composed of, for example, a plurality of kinds of buttons 72 and a controller 74 and are capable of accepting an operation of the counting apparatus 77 by a purified water manager or the like. Further, the notification display 76 is capable of displaying, for example, input information, operation information, and so on in addition to the counting result notified by the aforesaid notifying part 400.

Concretely, in the counting apparatus 77, the purified water supplied from the dividing device 78 first flows in the device 30 which makes the target flow therein. Then, a laser light having a 375 nm to 420 nm wavelength easily exciting riboflavin is radiated to the flowing purified water from a light emitting device 10 of the counting apparatus 77. Here, possible viable particles contained in the purified water are phytoplanktons besides bacteria, yeast, and mold described above. In order to detect whether or not the phytoplanktons exist in the purified water, the detection of an autofluorescence light 35e of chlorophyll or the like of a substance existing in their cells is used as an index. An excitation wavelength spectrum of the chlorophyll presents a distribution having a peak at an about 430 nm wavelength, and therefore, the wavelength of the laser light from the light emitting device 10 is suitably 400 nm to 450 nm.

Thereafter, in the counting apparatus 77, a scattered light, a Raman-scattered light, and the autofluorescence light are emitted to the surroundings due to an interaction of the radiated laser light with the purified water (water molecules) flowing in the device 30 which makes the target flow therein and with the target (the viable particle 35 or the non-viable particle 37), as described above (refer to FIG. 1). Then, these lights pass through a plurality of condensing lens systems 40, 80, 100 and devices which select the light based on the wavelength (devices 60, 70) to be detected by a light receiving devices (devices 90, 110). Further, as described above (refer to FIG. 8 and FIG. 9), regarding the Raman-scattered light and the autofluorescence light emitted from the purified water, most of the Raman-scattered light by the water is cut off by, for example, the long-pass filter 70 using a cutoff wavelength (for example, 490 nm) as its reference, while the autofluorescence light is transmitted. Incidentally, when chlorophyll is used as an index, the cutoff wavelength of the long-pass filter or the like is suitably about 600 nm. This is because an autofluorescence light spectrum of the chlorophyll presents a distribution having a peak at about 650 nm, and it is necessary to transmit lights having these wavelengths. Thereafter, the detection signals of the device 110 and the device 90 are transmitted to the autofluorescence light counting system 2. In the autofluorescence light counting system 2, it is confirmed in real time whether or not the viable particles 35 exist based on the transmitted data, and the viable particles 35 are counted for each particle size. Then, finally, the counting result is displayed by the notification display 76 or output to the outside.

According to the above-described embodiment of the apparatus, for example, by radiating the 405 nm laser light and using the autofluorescence light from chlorophyll in a cell of the viable particle in the purified water as an index, it is possible to easily excite an energy state of the riboflavin or chlorophyll. Further, a peak wavelength of the autofluorescence light of the chlorophyll is about 650 nm, while a peak wavelength of the Raman-scattered light by the water is about 465 nm. Therefore, by setting the cutoff wavelength serving as the reference of the long-pass filter 70 to 490 to 600 nm, efficient separation is possible, which can further improve counting accuracy of the viable particles.

Note that the device 70 of the light detecting system 1 is not limited to the long-pass filter 70 and may be formed by a dichroic mirror. For example, a dichroic mirror that transmits a light having a wavelength longer than the 490 nm (600 nm) cutoff wavelength and reflects a light having a wavelength shorter than the 490 nm (600 nm) cutoff wavelength may be provided. By providing such a dichroic mirror, a light having a wavelength shorter than 490 nm (mainly the scattered light from the viable particle 35 or the non-viable particle 37) is received by the photodiode 110, and a light having a wavelength longer than 490 nm (600 nm) (mainly the autofluorescence light 35e from the viable particle 35) is received by the photo multiplier tube 90.

Besides, regarding the devices 60, 70 of the light detecting system 1, the device 70 need not be installed on a subsequent stage of the device 60. Concretely, the device 60 and the device 70 may be installed in parallel so that light paths of the scattered light and the autofluorescence light become separate systems. In this case, a short-pass filter which transmits only a light whose wavelength is shorter than the 410 nm cutoff wavelength is used as the device 60. Then, the condensing lens optical systems which gather the scattered light and the autofluorescence light 35e from the flow cell, and the photodiode 110 which receives the scattered light and the first light receiving device 90 are installed in front of and at the back of the respective optical devices. For example, the device (short-pass filter) which reflects the scattered light is installed at a 90 degree position (horizontal plane) from the optical axis of the laser light 31, and the device (long-pass filter) which selects the autofluorescence light is installed at a 90 degree position (vertical plane) from the optical axis of the laser light 31. Consequently, owing to the device (short-pass filter) which reflects the scattered light, the photodiode 110 can detect mainly the scattered light from the viable particle 35 or the non-viable particle 37. Further, owing to the device (long-pass filter) which selects the autofluorescence light, the photo multiplier 90 can detect mainly the autofluorescence light 35e from the viable particle 35.

Further, by radiating the laser light 31 having a wavelength corresponding to an autofluorescent substance and providing the dichroic mirror which reflects the scattered light by the target and the long-pass filter which reduces the Raman-scattered light 33s by water or the like and transmits the autofluorescence light 35e from the viable particle 35, it is possible to improve counting accuracy of the viable particles 35.

As described above, according to this embodiment, by using the counting apparatus 77, regarding the purified water stored in the purified water basin 818, it is possible to determine in real time whether or not the viable particle 35 exists. Incidentally, in the determination on the presence/absence of the viable particles regarding the purified water as well, the detection of the autofluorescence light 35e is used as an index. Further, the autofluorescence light 35e is emitted from the autofluorescent substance necessary for metabolism occurring in a living organism, such as riboflavin, NAD(P)H, or chlorophyll in the cell of the viable particle 35 being a detection (measurement) target. Therefore, when as a result of the counting by the counting apparatus 77, it is confirmed that a prescribed number of the viable particles 35 or more exist in the purified water, the result is notified to the outside from a notifying device provided in the counting apparatus 77. For example, it is possible to output notifying sound from a speaker or output a notification signal for notifying the result to the central monitoring and controlling apparatus 880. The central monitoring and control apparatus 880 is capable of deciding a supply amount of the chlorine in real time based on the notification signal, and based on the decision contents, is capable of controlling the regulating valves in the chemical injection controlling apparatus 870. Therefore, when a prescribed number of the viable particles 35 or more exist in the purified water, it is possible to adjust a supply amount of the chlorine in real time.

Next, a purified water monitoring system including the counting apparatus 77 will be described.

[Purified Water Monitoring System Including Viable Particle Counting Apparatus]

Figure 20:
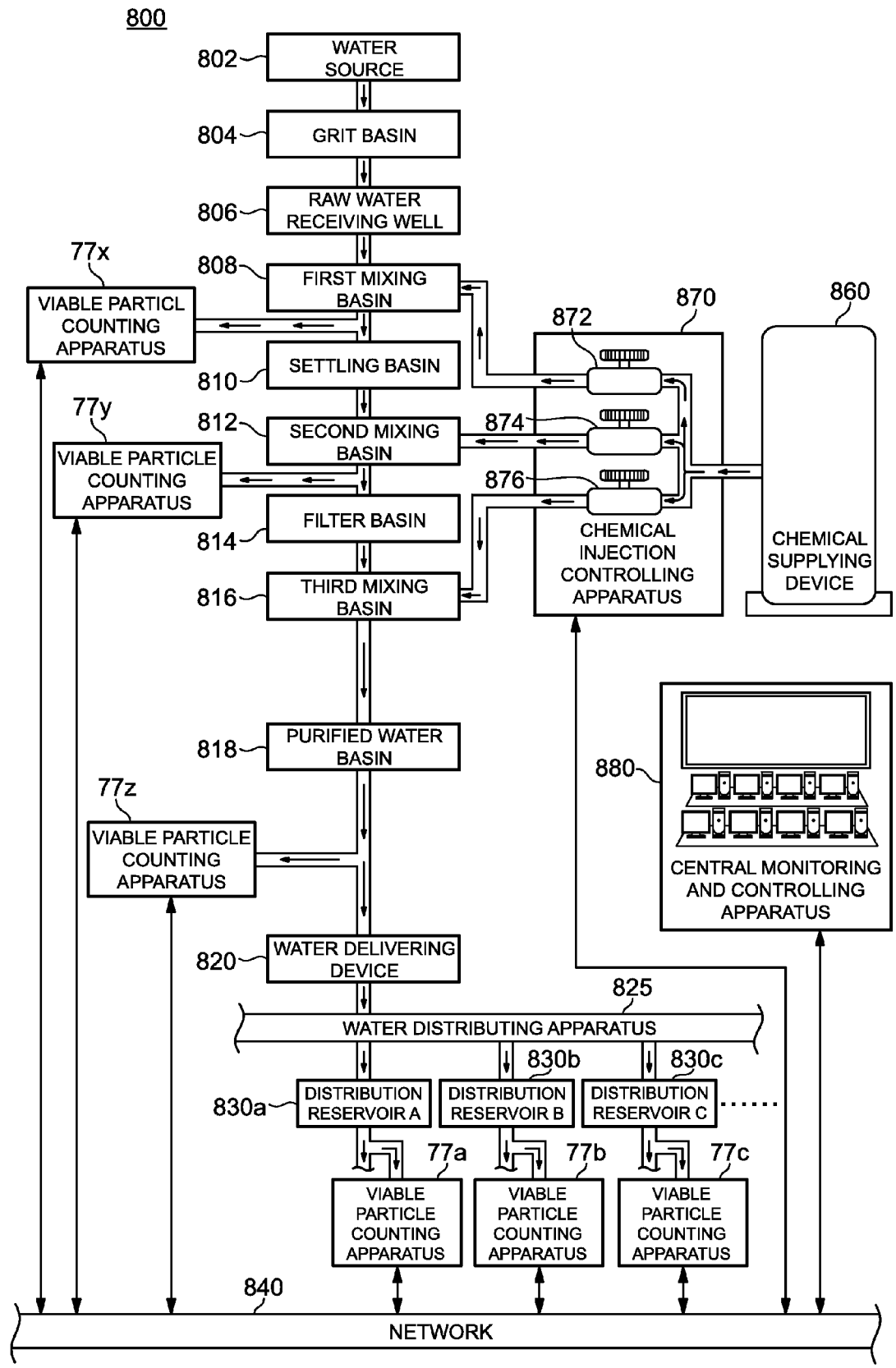
FIG. 20 is an explanatory diagram of a purified water monitoring system using the viable particle counting apparatus.

FIG. 20 is an explanatory diagram of the purified water monitoring system using the counting apparatus 77.

As illustrated in FIG. 20, the purified water monitoring system not only includes a counting apparatus 77z for inspecting the purified water stored in the purified water basin 818 but also performs the inspection of the chlorinated water by using the counting apparatus 77. Concretely, in order to inspect the water chlorinated in the first mixing basin 808, a counting apparatus 77x is provided between the first mixing basin 808 and the settling basin 810. Further, similarly, in order to inspect the water chlorinated in the second mixing basin 812, a counting apparatus 77y is provided between the second mixing basin 812 and the third mixing basin 816. Incidentally, regarding the counting apparatus 77x and the counting apparatus 77y, the water sent from the first mixing basin 808 and the second mixing basin 812 is also divided by the above-described dividing devices (dividing step), and it is determined whether or not the viable particle exists in the divided water, and when it is determined that the viable particle exists, the number of the viable particles is counted.

Further, in the purified water monitoring system, the target water is not limited to the water chlorinated by the water purifying system 800. After the manufactured purified water stored in the purified water basin is sent by the water pump 820 to be stored in the distribution reservoirs through the water distribution pipe 825, the determination on whether or not the viable particles exist is also performed for the purified water stored in the distribution reservoirs.

[Distribution Reservoirs]

In order to adjust a distribution amount of the purified water manufactured in the water purifying system 800, the purified water is temporarily stored in the distribution reservoirs 830. Note that the plural distribution reservoirs are provided via the water distribution pipe 825 as illustrated in FIG. 20. For example, a distribution reservoir A 830a, a distribution reservoir B 830b, a distribution reservoir C 803c, and so on are provided. In the purified water monitoring system, a counting apparatus 77a is installed for the distribution reservoir A 830a, a counting apparatus 77b is installed for the distribution reservoir B 830b, and a counting apparatus 77c is installed for the distribution reservoir C 830c, and the purified waters stored in the respective distribution reservoirs 830a, 830b, 830c are divided by dividing devices of the respective counting apparatuses 77a, 77b, 77c (dividing step). Then, regarding the divided purified waters, it is determined whether or not the viable particles exist, and when the viable particles exist, the number of the viable particles is counted.

[Network]

A network 840 connects the central monitoring and controlling apparatus 880 with the viable particle counting apparatuses 77x, 77y, 77z, 77a, 77b, 77c. Via this network 840, the determination results on the presence/absence of the viable particles transmitted from the respective counting apparatuses and count values of the viable particles are transmitted to the central monitoring and controlling apparatus 880. Incidentally, the central monitoring and controlling apparatus 880 may transmit control signals to the counting apparatuses. Concretely, the central monitoring and controlling apparatus 880 may transmit control signals for starting and finishing the inspection of the water at places where the counting apparatuses are provided, and may inspect the water in real time by remote-controlling the counting apparatuses.

By thus monitoring in real time the water at the places where the counting apparatuses are provided via the network

840, it is possible to adjust an amount of the chlorine necessary for the chlorination in real time. Incidentally, a control signal for controlling the adjustment of an amount of the chlorine for this chlorination is also transmitted from the central monitoring and controlling apparatus 880 via the network 840 to the chemical injection controlling apparatus 870, so that the flow rates in the regulating valves 872, 874, 876 are adjusted. When a problem is found in the purified water in or after the purified water basin 818, a regulating valve 878 (not illustrated) is controlled via the network 840. Consequently, it is possible to inject the chlorine to a spare water distribution pipe (not illustrated) for chlorination provided between the purified water basin 818 and the water pump 820.

As described above, being provided with the plural counting apparatuses 77, the purified water monitoring system is capable of the real-time inspection not only of the purified water (purified water basin 818) manufactured by the water purifying system 800 but also of the waters in the plural water distribution reservoirs. Concretely, the chlorinated water (the first mixing basin 808, the second mixing basin 812) can be inspected in real time. Further, based on the results of these inspections, the central monitoring and controlling apparatus 880 decides an injection amount of the chlorine in the chlorination. Further, when the control signal based on the decided injection amount is transmitted from the central monitoring and controlling apparatus 880, the regulating valves of the chemical injection controlling apparatus 870 are controlled based on the control signal.

Therefore, it is possible to confirm an increase/decrease of seaweeds, microorganisms, and so on due to a climate change based on the inspection using the plural counting apparatuses 77, and it is possible to adjust the injection amount of the chlorine according to the inspection result. Further, it is possible to prevent too large amount of the chlorine from being injected more than necessary. Accordingly, it is possible to reduce damage to the water distribution pipes and the generation of chlorination by-product (trihalomethane or the like) produced by the chlorination that affects a human body.

What is claimed is:

1. A viable particle counting apparatus comprising:
   a light emitting element which radiates a light toward a liquid containing a detection target, a wavelength of the light causing a peak wavelength of an autofluorescence light emitted from the target irradiated with the light and a peak wavelength of a Raman scattered light to be different from each other;
   an optical filter which reduces transmission of the Raman-scattered light emitted from the liquid out of lights emitted due to an interaction of the target or the liquid with the light radiated by the light emitting element and transmits the autofluorescence light emitted from the target; and
   a determining device which determines whether or not the target contained in the liquid is a viable particle, based on a light obtained after the Raman-scattered light is reduced by the optical filter.

2. The viable particle counting apparatus according to claim 1, further comprising:
   a dichroic mirror which reflects the scattered light emitted from the target and transmits the light including the autofluorescence light and the Raman-scattered light,
   wherein the determining device determines whether or not the target contained in the liquid is the viable particle, based on the light transmitted by dichroic mirror and having passed through the optical filter.

3. The viable particle counting apparatus according to claim 2, further comprising:
   a first light receiving device which receives the light having passed through the optical filter to output a first signal having an intensity corresponding to an amount of the received light;
   a second light receiving device which receives the light reflected by the dichroic mirror to output a second signal having an intensity corresponding to an amount of the received light;
   a signal outputting device which, when the intensity of the second signal output by the second light receiving device is equal to or larger than a predetermined threshold value, determines that the scattered light emitted from the target contained in the liquid is detected and outputs a detection signal; and
   a light shielding device which prevents a light incident from a place other than a light path from entering to the light path, which leads from the dichroic mirror to the first light receiving device through the optical filter,
   wherein, in the case where the detection signal is output by the signal outputting device, when the light is received by the first light receiving device at the same time as an instant when the scattered light emitted from the target contained in the liquid is received by the second light receiving device and the intensity of the first signal corresponding to the light received by the first light receiving device at the same time as the instant is equal to or larger than a predetermined threshold value, the determining device determines that the target contained in the liquid corresponding to the detection signal output by the signal outputting device is the viable particle.

4. The viable particle counting apparatus according to claim 1,
   wherein the predetermined wavelength of the light radiated by the light emitting element is 375 nm to 420 nm, and
   wherein a cutoff wavelength serving as a reference for the transmission of the light by the optical filter is 450 nm to 490 nm.

5. The viable particle counting apparatus according to claim 1, further comprising:
   a distributing device which distributes a dialysis fluid for blood dialysis or blood filtration; and
   a dividing device which makes part of the dialysis fluid distributed by the distributing device branch off as a liquid containing the detection target before the dialysis fluid is administered to a human body,
   wherein the light emitting element radiates a light with a predetermined wavelength toward the dialysis fluid made to branch off as the liquid by the dividing device, and
   wherein, based on the autofluorescence light out of lights emitted due to an interaction between the target contained in the dialysis fluid and the light radiated by the light emitting element, the determining device determines whether or not the target contained in the dialysis fluid is the viable particle.

6. The viable particle counting apparatus according to claim 1, further comprising:
   a dividing device which makes at least one of water under purification treatment and water whose purification treatment is finished branch off as the liquid containing the target to be detected,
   wherein the light emitting element radiates a light with a predetermined wavelength to the water made to branch off by the dividing device, and
   wherein the determining device determines whether or not the target contained in the purified water is the viable particle, based on the autofluorescence light out of lights emitted due to an interaction of the target contained in the water and the light radiated by the light emitting element.

7. The viable particle counting apparatus according to claim 6,
wherein the predetermined wavelength of the light radiated by the light emitting element is 375 nm to 450 nm, and
wherein a cutoff wavelength serving as a reference for the transmission of the light by the optical filter is 450 nm to 600 nm.

8. A dialysis fluid monitoring system comprising:
(A) a supplying apparatus which supplies a dialysis fluid for a plurality of people when there are a plurality of subjects undergoing an artificial dialysis;
(B) dialysis monitoring apparatuses which monitor information of the subjects and flows of blood and the dialysis fluid;
(C) an allocating device which allocates the dialysis fluid supplied by the supplying apparatus to the dialysis monitoring apparatuses installed corresponding to the respective subjects;
(D) a viable particle counting apparatus which is provided in at least one of the supplying apparatus and the plural dialysis monitoring apparatuses and which includes:
  (d1) a distributing device which distributes the dialysis fluid for blood dialysis or blood filtration;
  (d2) a dividing device which makes part of the dialysis fluid distributed by the distributing device branch off as a liquid containing a detection target before the dialysis fluid is administered to a human body;
  (d3) a light emitting element which radiates a light toward the liquid, a wavelength of the light causing a peak wavelength of an autofluorescence light emitted from the target irradiated with the light and a peak wavelength of a Raman-scattered light to be different from each other;
  (d4) an optical filter which reduces transmission of the Raman-scattered light emitted from the dialysis fluid out of lights emitted due to an interaction of the target or the dialysis fluid with the light radiated by the light emitting element and transmits the autofluorescence light emitted from the target; and
  (d5) a determining device which, regarding the dialysis fluid supplied from the supplying apparatus or the dialysis fluid made to branch off to the dialysis monitoring apparatuses, determines whether or not the target contained in the dialysis fluid is a viable particle, based on the autofluorescence light out of lights obtained after the Raman-scattered light is reduced by the optical filter and emitted due to an interaction of the target contained in the dialysis fluid with the light radiated by the light emitting element; and
(E) a notifying device which notifies a result of the determination by the viable particle counting apparatus.

9. The dialysis fluid monitoring system according to claim 8,
wherein the viable particle counting apparatus is provided for each of the dialysis monitoring apparatuses.

10. A purified water monitoring system comprising:
(A) a purifying device which purifies water containing a target by a plural kinds of purification treatments in a plural purifying basins;
(B) a water delivering device which delivers the water having undergone the plural kinds of purification treatments by the purifying device to at least one distribution reservoir; and
(C) a viable particle counting apparatus which is provided in at least one place between the purifying basin where the purification treatment is first performed and the distribution reservoir and which includes:
  (c1) a dividing device which makes at least one of the water under the purification treatment and the water having undergone the purification treatment branch off as a liquid containing the target to be detected;
  (c2) a light emitting element which radiates a light toward the water made to branch off by the dividing device, a wavelength of the light causing a peak wavelength of an autofluorescence light emitted from the target irradiated with the light and a peak wavelength of a Raman-scattered light to be different from each other;
  (c3) an optical filter which reduces transmission of the Raman-scattered light emitted from the liquid out of lights emitted due to an interaction of the target or the water with the light radiated by the light emitting element and transmits the autofluorescence light emitted from the target; and
  (c4) a determining device which determines whether or not the target contained in the water made to branch off by the dividing device is a viable particle, based on the autofluorescence light out of lights obtained after the Raman-scattered light is reduced by the optical filter and emitted due to an interaction of the target contained in the water with the light radiated by the light emitting element; and
(D) a notifying device which notifies a result of the determination by the viable particle counting apparatus.

11. The purified water monitoring system according to claim 10, further comprising:
a supplying device which supplies chemicals used for the purification treatments by the purifying device;
an injecting device which injects the chemicals supplied by the supplying device;
an amount controlling device which controls an injection amount of the chemicals injected by the injecting device; and
a system controlling apparatus which instructs the control by the amount controlling device and controls water delivery in the purification treatments,
wherein the system controlling apparatus instructs the control by the amount controlling device based on the determination result of the viable particle counting apparatus.

12. A viable particle counting method comprising:
a light emitting step of radiating a light with a predetermined wavelength toward a liquid containing a detection target, a wavelength of the light causing a peak wavelength of an autofluorescence light emitted from the target irradiated with the light and a peak wavelength of a Raman-scattered light to be different from each other;
a transmitting step of reducing transmission of the Raman-scattered light emitted from the liquid out of lights emitted due to an interaction of the target or the liquid with the light radiated in the light emitting step and transmitting the autofluorescence light emitted from the target; and
a determining step of determining whether or not the target contained in the liquid is a viable particle, based on a light obtained after the Raman-scattered light is reduced by the transmitting step.

13. The viable particle counting method according to claim 12, further comprising:

a reflecting step of reflecting a scattered light emitted from the target and transmitting the light including the autofluorescence light and the Raman-scattered light, wherein, in the determining step, it is determined whether or not the target contained in the liquid is the viable particle, based on the light transmitted in the reflecting step and having passed through the transmitting step.

14. The viable particle counting method according to claim 13, further comprising:

a first light receiving step of receiving the light having passed through the transmitting step to output a first signal having an intensity corresponding to an amount of the received light;

a second light receiving step of receiving the light reflected in the reflecting step to output a second signal having an intensity corresponding to an amount of the received light;

a signal outputting step of, when the intensity of the second signal output in the second light receiving step is equal to or larger than a predetermined threshold value, determining that the scattered light emitted from the target contained in the liquid is detected and outputting a detection signal; and a light shielding step of preventing a light incident from a place other than a light path from entering to the light path, which leads from the reflecting step to the first light receiving step through the transmitting step, wherein, in the case where the detection signal is output in the signal outputting step, when the light is received in the first light receiving step at the same time as an instant when the scattered light emitted from the target contained in the liquid is received in the second light receiving step and the intensity of the first signal corresponding to the light received in the first light receiving step at the same time as the instant is equal to or larger than a predetermined threshold value, it is determined in the determining step that the target contained in the liquid corresponding to the detection signal output in the signal outputting step is the viable particle.

15. The viable particle counting method according to claim 12, wherein the predetermined wavelength of the light radiated in the light emitting step is 375 nm to 420 nm, and wherein a cutoff wavelength serving as a reference for the transmission of the light in the transmitting step is 450 nm to 490 nm.

* * * * *